(12) United States Patent
Ohashi

(10) Patent No.: US 11,605,192 B2
(45) Date of Patent: Mar. 14, 2023

(54) SKELETON MODEL UPDATE APPARATUS, SKELETON MODEL UPDATE METHOD, AND PROGRAM

(71) Applicant: SONY INTERACTIVE ENTERTAINMENT INC., Tokyo (JP)

(72) Inventor: Yoshinori Ohashi, Tokyo (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 0 days.

(21) Appl. No.: 17/278,648

(22) PCT Filed: Jun. 21, 2019

(86) PCT No.: PCT/JP2019/024819
§ 371 (c)(1),
(2) Date: Mar. 22, 2021

(87) PCT Pub. No.: WO2020/070928
PCT Pub. Date: Apr. 9, 2020

(65) Prior Publication Data
US 2021/0295580 A1    Sep. 23, 2021

(30) Foreign Application Priority Data
Oct. 3, 2018  (WO) .................. PCT/JP2018/036973

(51) Int. Cl.
*G06T 13/40* (2011.01)
*A63F 13/212* (2014.01)
*A63F 13/25* (2014.01)

(52) U.S. Cl.
CPC ............ *G06T 13/40* (2013.01); *A63F 13/212* (2014.09); *A63F 13/25* (2014.09)

(58) Field of Classification Search
CPC ......... G06T 13/40; A63F 13/212; A63F 13/25
See application file for complete search history.

(56) References Cited

U.S. PATENT DOCUMENTS

| 2017/0003738 A1* | 1/2017 | Silkin | A63F 13/214 |
| 2018/0122125 A1* | 5/2018 | Brewster | G06T 13/40 |
| 2022/0035443 A1* | 2/2022 | Winold | A61B 5/1123 |

FOREIGN PATENT DOCUMENTS

| JP | 9-153151 A | 6/1997 |
| JP | 10-302085 A | 11/1998 |

(Continued)

OTHER PUBLICATIONS

International Preliminary Report on Patentability dated Mar. 23, 2021, from PCT/JP2019/024819, 13 sheets.

(Continued)

*Primary Examiner* — Yu Chen
(74) *Attorney, Agent, or Firm* — Katten Muchin Rosenman LLP

(57) ABSTRACT

A posture data acquisition section acquires posture data indicating a posture of a target node included in a skeleton model of a tree structure. An initial position determination section determines a position to which the target node is to move on the basis of the position data. The initial position determination section determines an initial position of a parent node of the target node in Forward and Backward Reaching Inverse Kinematics (FABRIK) computing on the basis of the position to which the target node is to move and a given posture of the skeleton model. A posture update section updates a posture of the skeleton model by executing the FABRIK computing including determination of a new position of the parent node on the basis of the position to which the target node is to move and the initial position of the parent node.

5 Claims, 12 Drawing Sheets

(56) References Cited

FOREIGN PATENT DOCUMENTS

| JP | 2010-014712 A | 1/2010 |
| JP | 2011-177300 A | 9/2011 |
| JP | 2015-011714 A | 1/2015 |
| JP | 2018-128851 A | 8/2018 |

OTHER PUBLICATIONS

International Search Report and Written Opinion dated Sep. 17, 2019, from PCT/JP2019/024819, 9 sheets.
Decision to Grant a Patent dated Feb. 22, 2022, from Japanese Patent Application No. 2020-549959, 2 sheets.

* cited by examiner

SKELETON MODEL UPDATE APPARATUS, SKELETON MODEL UPDATE METHOD, AND PROGRAM

TECHNICAL FIELD

The present invention relates to a skeleton model update apparatus, a skeleton model update method, and a program.

BACKGROUND ART

There is known a technology for determining a posture of a skeleton model made to correspond to a user on the basis of data indicating postures of a plurality of trackers attached to the user.

In the technology, for example, data indicating the postures of the trackers made to correspond to part of a plurality of nodes included in the skeleton model is repeatedly acquired. The posture of the skeleton model of a tree structure including the plurality of nodes and a plurality of bones is repeatedly determined on the basis of the acquired data.

A technology of Forward and Backward Reaching Inverse Kinematics (FABRIK) computing that is a kind of inverse kinematics (IK) computing is also known. FIGS. 4 and 5 schematically depict an example of FABRIK computing performed on a node group that contains four nodes.

In the FABRIK computing, forward reaching phase processing is first executed. As depicted in FIG. 4, in the forward reaching phase processing, first, a node at a position P(c1) moves to a position T1 which is identified on the basis of data indicating a posture of a tracker made to correspond to the node and to which the node is to move. The node made to correspond to the tracker will be referred to as "target node," hereinafter. In FIG. 4, a position of the target node after movement is denoted as P(c2). A parent node of the target node then moves from a position P(p1) to a position P(p2). It is noted here that the position P(p2) is a position apart from the position P(c2) by a length d1 between the position P(p1) and the position P(c1) in a direction from the position P(c2) to the position P(p1). The length between the two nodes is, therefore, kept constant. Likewise, a node at a position (o1) moves to a position P(o2), and a node at a position P(n1) moves to a position P(n2), hereinafter.

Subsequently, backward reaching phase processing is executed. As illustrated in FIG. 5, in the backward reaching phase processing, the node most apart from the target node moves from the position P(n2) to a position P(n3). It is noted here that the position P(n3) is the same position as the position P(n1) of the node at a time of starting the FABRIK computing. A child node of the node moves from a position P(o2) to a position P(o3). It is noted here that the position P(o3) is a position apart from the position P(n3) by a length d3 between the position P(o1) and the position P(n1) in a direction from the position P(n3) to the position P(o2). The length between the two nodes is, therefore, kept constant. Likewise, a node at the position P(p2) moves to a position P(p3), and a node at the position P(c2) moves to a position P(c3), hereinafter.

The forward reaching phase and the backward reaching phase are repeatedly executed until a length between the position of the target node and the position T1 is equal to or smaller than a predetermined threshold. It is noted that the FABRIK computing is ended when the forward reaching phase and the backward reaching phase are repeatedly executed a predetermined number of times (for example, ten times) even if the length between the position of the target node and the position T1 is not equal to or smaller than the predetermined threshold.

As described so far, in the FABRIK computing, the posture of the skeleton model is determined by a simple algorithm based on the position to which the target node is to move, current positions of the respective nodes, and lengths of given nodes.

SUMMARY

Technical Problems

As described above, the posture of the skeleton model is determined by the simple algorithm in the FABRIK computing; as a result, however, joints are not bent in natural directions and the posture of the skeleton model which is impossible as that of the human body is sometimes determined.

Further, in a case of determining the posture by the FABRIK computing, information regarding a rotation of each hand about an axis in an arm direction is not reflected in a rotation of an elbow about the axis in the arm direction although this information can be acquired from trackers.

Further, in the FABRIK computing performed on the skeleton model of the tree structure, it is necessary to execute independent forward reaching phase processing on a node group that contains a target node with each of a plurality of target nodes used as a starting point. Owing to this, the forward reaching phase processing sometimes causes overall postures of a plurality of nodes, for example, from the chest to the shoulders in the vicinity of junctions of the skeleton model of the tree structure to get greatly distorted although the overall postures are not supposed to get greatly distorted.

The present invention has been achieved in light of the problems, and one object of the present invention is to provide a skeleton model update apparatus, a skeleton model update method, and a program capable of improving adequacy of a determination result of a posture of a skeleton model by using Forward and Backward Reaching Inverse Kinematics computing.

Solution to Problems

To solve the problems, a skeleton model update apparatus according to the present invention includes a posture data acquisition section that acquires posture data indicating a posture of a target node included in a skeleton model of a tree structure, a position determination section that determines a position to which the target node is to move on the basis of the posture data, an initial position determination section that determines an initial position of a parent node of the target node in Forward and Backward Reaching Inverse Kinematics computing including determination of a new position of the parent node on condition that a length between the target node and the parent node is kept constant and based on the position to which the target node is to move and a current position of the parent node of the target node, on the basis of the position to which the target node is to move and a given posture of the skeleton model, and a posture update section that updates a posture of the skeleton model by executing the Forward and Backward Reaching Inverse Kinematics computing including the determination of the new position of the parent node based on the position to which the target node is to move and the initial position of the parent node.

Further, another skeleton model update apparatus according to the present invention includes a posture data acquisition section that acquires posture data indicating a posture of a target node included in a skeleton model of a tree structure, a posture update section that updates a posture of the skeleton model by executing Forward and Backward Reaching Inverse Kinematics computing, a rotation identification section that identifies a rotation of the target node about an axis that is a bone connecting the target node to the parent node of the target node on the basis of the posture data, and a rotation determination section that determines a rotation of the parent node on the basis of the rotation of the target node.

Further, yet another skeleton model update apparatus according to the present invention includes a posture data acquisition section that acquires posture data indicating a posture of a first target node and a posture of a second target node, the first and second target nodes being included in a skeleton model of a tree structure, a first posture update section that performs update of postures of a first node group that contains nodes including the first target node and connected to one another by forward reaching phase processing in Forward and Backward Reaching Inverse Kinematics computing, on the first node group on the basis of the posture data, a second posture update section that performs update of postures of a second node group that contains nodes including the second target node and connected to one another by the forward reaching phase processing in the Forward and Backward Reaching Inverse Kinematics computing, on the second node group on the basis of the posture data, a third posture update section that updates postures of a plurality of nodes including a node included in the first node group and closest to a junction included in the skeleton model and a node included in the second node group and closest to a junction included in the skeleton model after updating the first node group and the second node group, and a fourth posture update section that updates a posture of the skeleton model by backward reaching phase processing in the Forward and Backward Reaching Inverse Kinematics computing.

Further, according to one aspect of the present invention, the skeleton model update apparatus further includes an estimation section that estimates a pivoting foot on the basis of the posture data, and a determination section that determines an initial position of a lumbar node in the Forward and Backward Reaching Inverse Kinematics computing on the basis of a position of the pivoting foot.

In this aspect, the estimation section may further estimate whether a user is in a seated posture or a standing posture, and the estimation section may estimate the pivoting foot in a case of estimating that the user is in the standing posture.

Further, a skeleton model update method according to the present invention includes a step of acquiring posture data indicating a posture of a target node included in a skeleton model of a tree structure, a step of determining a position to which the target node is to move on the basis of the posture data, a step of determining an initial position of a parent node of the target node in Forward and Backward Reaching Inverse Kinematics computing including determination of a new position of the parent node on condition that a length between the target node and the parent node is kept constant and based on the position to which the target node is to move and a current position of the parent node of the target node, on the basis of the position to which the target node is to move and a given posture of the skeleton model, and a step of updating a posture of the skeleton model by executing the Forward and Backward Reaching Inverse Kinematics computing including the determination of the new position of the parent node based on the position to which the target node is to move and the initial position of the parent node.

Further, another skeleton model update method according to the present invention includes a step of acquiring posture data indicating a posture of a target node included in a skeleton model of a tree structure, a step of updating a posture of the skeleton model by executing Forward and Backward Reaching Inverse Kinematics computing, a step of identifying a rotation of the target node about an axis that is a bone connecting the target node to the parent node of the target node on the basis of the posture data, and a step of determining a rotation of the parent node on the basis of the rotation of the target node.

Further, yet another skeleton model update method according to the present invention includes a step of acquiring posture data indicating a posture of a first target node and a posture of a second target node, the first and second target nodes being included in a skeleton model of a tree structure, a step of performing update of postures of a first node group that contains nodes including the first target node and connected to one another by forward reaching phase processing in Forward and Backward Reaching Inverse Kinematics computing, on the first node group on the basis of the posture data, a step of performing update of postures of a second node group that contains nodes including the second target node and connected to one another by the forward reaching phase processing in the Forward and Backward Reaching Inverse Kinematics computing, on the second node group on the basis of the posture data, a step of updating postures of a plurality of nodes including a node included in the first node group and closest to a junction included in the skeleton model and a node included in the second node group and closest to a junction included in the skeleton model after updating the first node group and the second node group, and a step of updating a posture of the skeleton model by backward reaching phase processing in the Forward and Backward Reaching Inverse Kinematics computing.

Further, a program according to the present invention causes a computer to execute a procedure of acquiring posture data indicating a posture of a target node included in a skeleton model of a tree structure, a procedure of determining a position to which the target node is to move on the basis of the posture data, a procedure of determining an initial position of a parent node of the target node in Forward and Backward Reaching Inverse Kinematics computing including determination of a new position of the parent node on condition that a length between the target node and the parent node is kept constant and based on the position to which the target node is to move and a current position of the parent node of the target node, on the basis of the position to which the target node is to move and a given posture of the skeleton model, and a procedure of updating a posture of the skeleton model by executing the Forward and Backward Reaching Inverse Kinematics computing including the determination of the new position of the parent node based on the position to which the target node is to move and the initial position of the parent node.

Further, another program according to the present invention causes a computer to execute a procedure of acquiring posture data indicating a posture of a target node included in a skeleton model of a tree structure, a procedure of updating a posture of the skeleton model by executing Forward and Backward Reaching Inverse Kinematics computing, a procedure of identifying a rotation of the target node about an axis that is a bone connecting the target node to the parent node of the target node on the basis of the posture data, and a procedure of determining a rotation of the parent node on the basis of the rotation of the target node.

Further, yet another program according to the present invention causes a computer to execute a procedure of acquiring posture data indicating a posture of a first target node and a posture of a second target node, the first and second target nodes being included in a skeleton model of a tree structure, a procedure of performing update of postures of a first node group that contains nodes including the first target node and connected to one another by forward reaching phase processing in Forward and Backward Reaching Inverse Kinematics computing, on the first node group on the basis of the posture data, a procedure of performing update of postures of a second node group that contains nodes including the second target node and connected to one another by the forward reaching phase processing in the Forward and Backward Reaching Inverse Kinematics computing, on the second node group on the basis of the posture data, a procedure of updating postures of a plurality of nodes including a node included in the first node group and closest to a junction included in the skeleton model and a node included in the second node group and closest to a junction included in the skeleton model after updating the first node group and the second node group, and a procedure of updating a posture of the skeleton model by backward reaching phase processing in the Forward and Backward Reaching Inverse Kinematics computing.

DESCRIPTION OF EMBODIMENT

Figure 1:
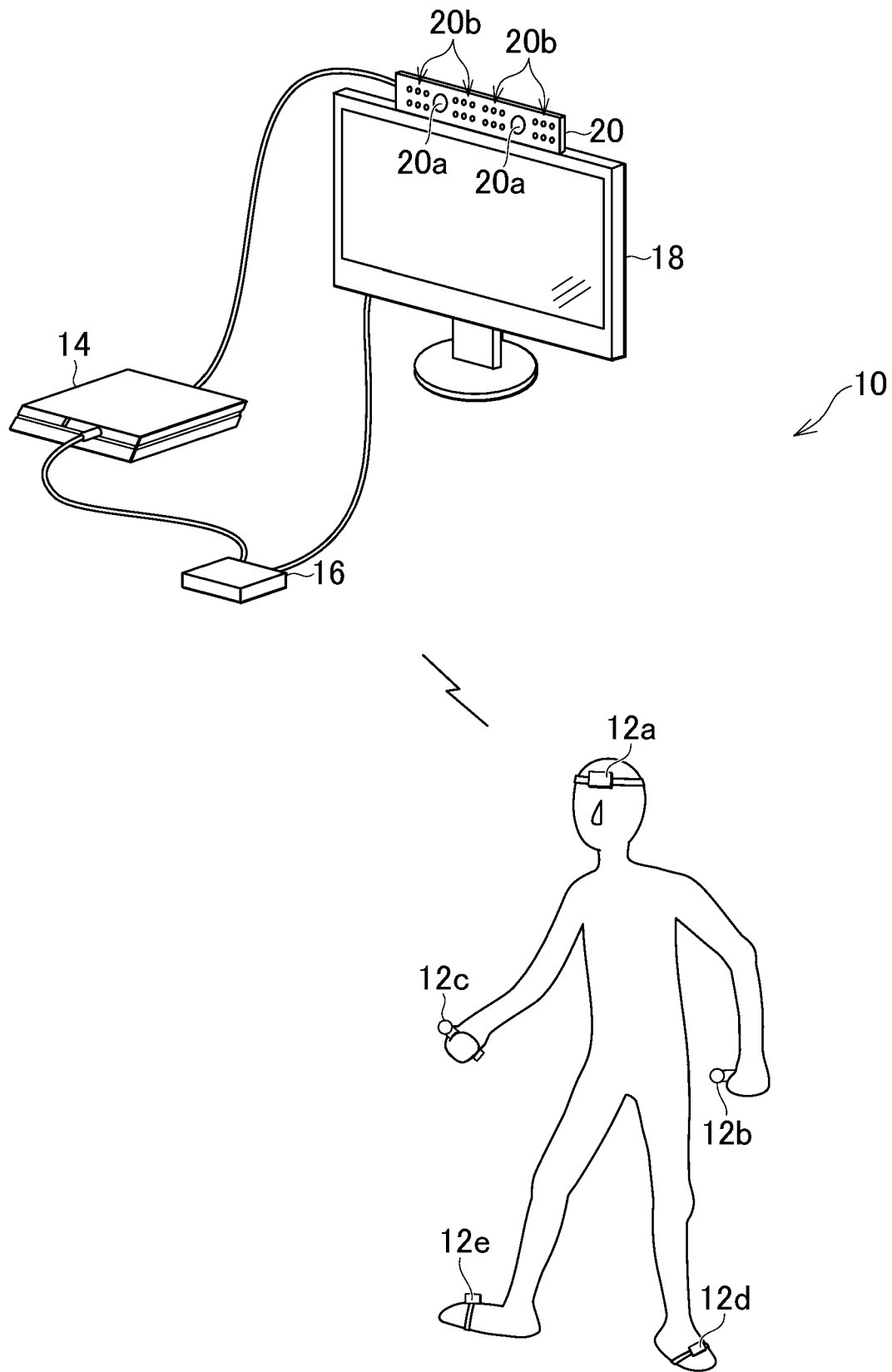
FIG. 1 is a configuration diagram depicting an example of an entertainment system according to an embodiment of the present invention.
Figure 2:
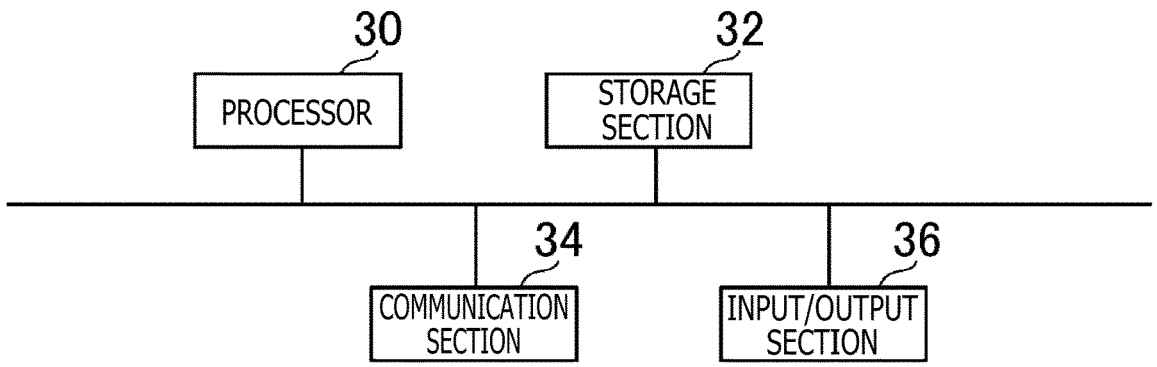
FIG. 2 is a configuration diagram depicting an example of an entertainment apparatus according to the embodiment of the present invention.

FIG. 1 is a diagram depicting an example of configurations of an entertainment system 10 according to an embodiment of the present invention. FIG. 2 is a diagram depicting an example of configurations of an entertainment apparatus 14 according to the present embodiment.

As depicted in FIG. 1, the entertainment system 10 according to the present embodiment includes a plurality of trackers 12 (trackers 12a to 12e in the example of FIG. 1), the entertainment apparatus 14, a relay apparatus 16, a display 18, and a camera microphone unit 20.

The trackers 12 according to the present embodiment are devices that, for example, track positions and directions of the trackers 12. Each of the trackers 12 may be configured here with, for example, various sensors such as a camera, an inertial measurement unit (IMU), a geomagnetic sensor (azimuth sensor), an acceleration sensor, a motion sensor, and a GPS (Global Positioning System) module. In addition, each of the trackers 12 may identify the posture of the tracker 12 on the basis of sensing data that is measurement results by the sensors provided in the tracker 12.

Alternatively, each of the trackers 12 may identify the posture of the tracker 12 on the basis of, for example, an image captured by a camera 20a included in the camera microphone unit 20, to be described later, and containing an image of the tracker 12.

In the present embodiment, the trackers 12a, 12b, 12c, 12d, and 12e are attached to a head, a left hand, a right hand, a left foot, and a right foot of a user, respectively. As depicted in FIG. 1, the trackers 12b and 12c may be here grasped by user's hands. In the present embodiment, postures identified by the trackers 12a, 12b, 12c, 12d, and 12e correspond to postures of the head, the left hand, the right hand, the left foot, and the right foot of the user, respectively. In this way, in the present embodiment, the plurality of trackers 12 identify the postures of a plurality of regions included in a user's body.

Examples of the entertainment apparatus 14 according to the present embodiment include computers such as a game console, a DVD (Digital Versatile Disc) player, a Blu-ray (registered trademark) player. The entertainment apparatus 14 according to the present embodiment generates a video picture and a sound by, for example, execution of a game program or reproduction of a content stored or recorded in an optical disk. The entertainment apparatus 14 according to the present embodiment then outputs a video picture signal representing the generated video picture and an audio signal representing the generated sound to the display 18 via the relay apparatus 16.

As depicted in, for example, FIG. 2, the entertainment apparatus 14 according to the present embodiment includes a processor 30, a storage section 32, a communication section 34, and an input/output section 36.

The processor 30 is a program control device such as a CPU (Central Processing Unit) operating in accordance with, for example, a program installed in the entertainment apparatus 14. The processor 30 according to the present embodiment also includes a GPU (Graphics Processing Unit) that draws an image on a frame buffer on the basis of a graphics command and data supplied from the CPU.

The storage section 32 is, for example, storage elements such as a ROM (Read-Only Memory) and a RAM (Random Access Memory) or a hard disk drive. A program and the like executed by the processor 30 are stored in the storage section 32. Further, an area of the frame buffer where an image is drawn by the GPU is allocated in the storage section 32 according to the present embodiment.

The communication section 34 is, for example, a communication interface such as a wireless LAN (Local Area Network) module.

The input/output section 36 is an input/output port such as an HDMI (registered trademark) (High-Definition Multimedia Interface) port or a USB (Universal Serial Bus) port.

The relay apparatus 16 according to the present embodiment is a computer that relays the video picture signal and the audio signal output from the entertainment apparatus 14 and that outputs the video picture signal and the audio signal to the display 18.

The display 18 according to the present embodiment is, for example, a liquid crystal display, and displays thereon the video picture represented by the video picture signal output from the entertainment apparatus 14.

The camera microphone unit 20 according to the present embodiment includes, for example, the camera 20a that outputs an image obtained by imaging a subject to the entertainment apparatus 14, and a microphone 20b that acquires a surrounding sound, converts the sound into audio data, and outputs the audio data to the entertainment apparatus 14. Further, the camera 20a according to the present embodiment is a stereo camera.

The trackers 12 and the relay apparatus 16 are configured to be capable of mutually transmitting and receiving data by, for example, wireless communication. The entertainment apparatus 14 and the relay apparatus 16 are connected to each other via, for example, an HDMI cable or a USB cable, and configured to be capable of mutually transmitting and receiving data. The relay apparatus 16 and the display 18 are connected to each other via, for example, an HDMI cable. The entertainment apparatus 14 and the camera microphone unit 20 are connected to each other via, for example, an AUX (Auxiliary) cable.

Figure 3:
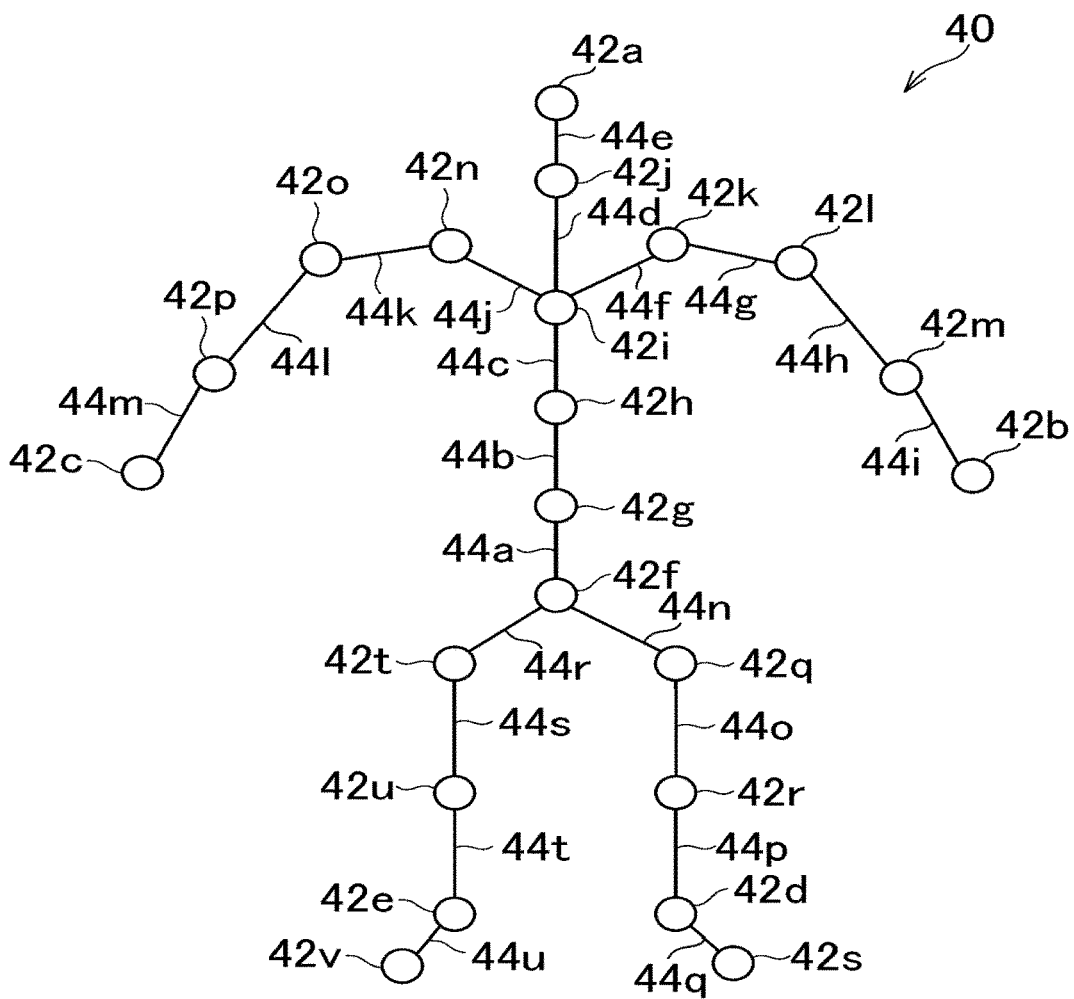
FIG. 3 is a diagram depicting an example of a skeleton model.

In the present embodiment, at a time of, for example, executing a game program by the entertainment apparatus 14, various types of processing such as game processing according to postures of the plurality of regions included in the user's body in a skeleton model 40 depicted in FIG. 3 are executed. A video picture according to a result of the processing is then displayed on, for example, the display 18. For example, a video picture of a polygon model of a player object according to a posture of the skeleton model 40 is displayed on the display 18.

As depicted in FIG. 3, the skeleton model 40 according to the present embodiment includes a head node 42a, a left hand node 42b, a right hand node 42c, a left foot node 42d, and a right foot node 42e. The head node 42a corresponds to the user's head to which the tracker 12a is attached. The left hand node 42b corresponds to the user's left hand to which the tracker 12b is attached. The right hand node 42c corresponds to the user's right hand to which the tracker 12c is attached. The left foot node 42d corresponds to the user's left foot to which the tracker 12d is attached. The right foot node 42e corresponds to the user's right foot to which the tracker 12e is attached.

The skeleton model 40 also includes a pelvis node 42f, a first spine node 42g, a second spine node 42h, a third spine node 42i, and a neck node 42j, in addition to the nodes 42 described above. In the present embodiment, the pelvis node 42f, for example, plays a role as a root node in the overall skeleton model 40. In addition, in the present embodiment, the pelvis node 42f, for example, corresponds to a lumbar node.

Further, the skeleton model 40 also includes a left clavicle node 42k, a left upper arm node 42l, a left front arm node 42m, a right clavicle node 42n, a right upper arm node 42o, and a right front arm node 42p.

Further, the skeleton model 40 also includes a left femoral region node 42q, a left calf node 42r, a left thenar node 42s, a right femoral region node 42t, a right calf node 42u, and a right thenar node 42v.

As depicted in FIG. 3, the pelvis node 42f is connected to the first spine node 42g by a bone 44a. Further, the first spine node 42g is connected to the second spine node 42h by a bone 44b. Further, the second spine node 42h is connected to the third spine node 42i by a bone 44c. Further, the third spine node 42i is connected to the neck node 42j by a bone 44d. Further, the neck node 42j is connected to the head node 42a by a bone 44e.

Further, the third spine node 42i is connected to the left clavicle node 42k by a bone 44f. Further, the left clavicle node 42k is connected to the left upper arm node 42l by a bone 44g. Further, the left upper arm node 42l is connected to the left front arm node 42m by a bone 44h. Further, the left front arm node 42m is connected to the left hand node 42b by a bone 44i.

Further, the third spine node 42i is connected to the right clavicle node 42n by a bone 44j. Further, the right clavicle node 42n is connected to the right upper arm node 42o by a bone 44k. Further, the right upper arm node 42o is connected to the right front arm node 42p by a bone 44l. Further, the right front arm node 42p is connected to the right hand node 42c by a bone 44m.

Further, the pelvis node 42f is connected to the left femoral region node 42q by a bone 44n. Further, the left femoral region node 42q is connected to the left calf node 42r by a bone 44o. Further, the left calf node 42r is connected to the left foot node 42d by a bone 44p. Further, the left foot node 42d is connected to the left thenar node 42s by a bone 44q.

Further, the pelvis node 42f is connected to the right femoral region node 42t by a bone 44r. Further, the right femoral region node 42t is connected to the right calf node 42u by a bone 44s. Further, the right calf node 42u is connected to the right foot node 42e by a bone 44t. Further, the right foot node 42e is connected to the right thenar node 42v by a bone 44u.

FIG. 3 depicts the skeleton model 40 in a basic posture (here, what is generally called an A pose posture with feet are open and the arms are obliquely down) that is the skeleton model 40 in an initial state.

In addition, in the present embodiment, body tracking, for example, based on the postures identified by the plurality of trackers 12 can be performed.

Determination of a position relative to a reference position in the initial state and a direction relative to a reference direction in the initial state, for example, is executed here for each of the plurality of nodes 42 included in the skeleton model 40. In addition, determination of a direction relative to a reference direction in the initial state is executed for each of a plurality of bones 44 included in the skeleton model 40.

A posture of the head node 42a, for example, can be determined here on the basis of data indicating a posture identified for the tracker 12a. Likewise, a posture of the left hand node 42b can be determined on the basis of data indicating a posture identified for the tracker 12b. Further, a posture of the right hand node 42c can be determined on the basis of data indicating a posture identified for the tracker 12c. Further, a posture of the left foot node 42d can be determined on the basis of data indicating a posture identified for the tracker 12d. Further, a posture of the right foot node 42e can be determined on the basis of data indicating a posture identified for the tracker 12e.

Further, a posture of the pelvis node 42f can be similarly determined on the basis of, for example, the determined posture of the head node 42a. Estimation of the posture of the pelvis node 42f by using a learned machine learning model may be executed here on the basis of, for example, the postures identified for the trackers 12a to 12e. Likewise, a posture of the third spine node 42i can also be determined.

It is then considered to determine positions and directions of the remaining nodes 42 and directions of the bones 44 by Forward and Backward Reaching Inverse Kinematics (FABRIK) computing on the basis of determination results and estimation results so far. For example, the head node 42a, the left hand node 42b, the right hand node 42c, the left foot node 42d, and the right foot node 42e correspond here to effectors in the FABRIK. The positions and the directions of the nodes 42 and the directions of the bones 44 included in the skeleton model 40 are then determined according to motions of the effectors.

Figure 4:
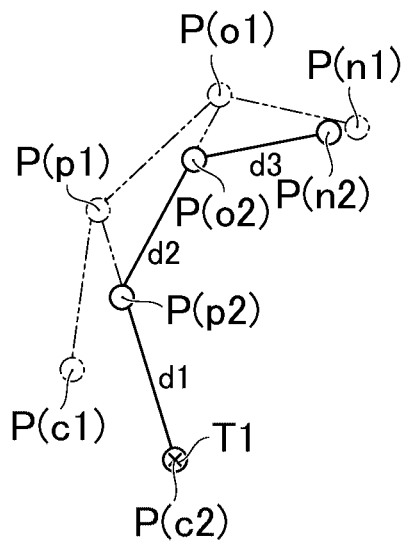
FIG. 4 is a diagram schematically depicting an example of a forward reaching phase in FABRIK computing.
Figure 5:
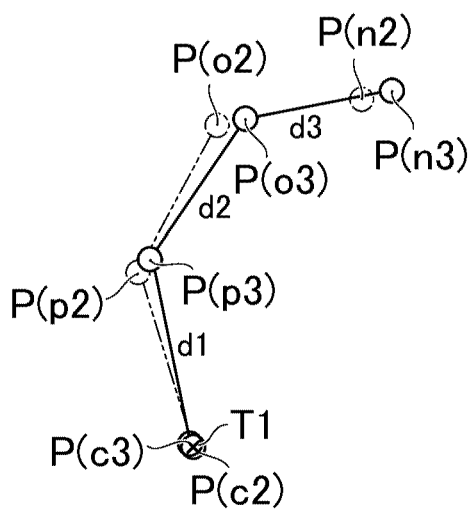
FIG. 5 is a diagram schematically depicting an example of a backward reaching phase in FABRIK computing.

FIGS. 4 and 5 are diagrams schematically depicting an example of FABRIK computing. By way of example, FIGS. 4 and 5 depict the FABRIK computing executed for the right hand node 42c, the right clavicle node 42n, the right upper arm node 42o, and the right front arm node 42p.

In FIG. 4, current positions of the right hand node 42c, the right clavicle node 42n, the right upper arm node 42o, and the right front arm node 42p in the skeleton model 40 are denoted as P(c1), P(n1), P(o1), and P(p1), respectively. It is also assumed that lengths of the bones 44m, 44l, 44k, and 44j are d1, d2, and d3, respectively.

It is assumed that the position T1 to which the right hand node 42c is to move is identified on the basis of a measurement result of the tracker 12c under these circumstances.

A forward reaching phase in the FABRIK computing will be described hereinafter with reference to FIG. 4.

In the forward reaching phase, the right hand node 42c moves first to the position T1. In FIG. 4, a position of the right hand node 42c after movement is denoted as P(c2). The right front arm node 42p then moves to the position P(p2) apart from the position P(c2) by the length d1 in the direction from the position P(c2) to the position P(p1). The right upper arm node 42o then moves to the position P(o2) apart from the position P(p2) by the length d2 in the direction from the position P(p2) to the position P(o1). The right clavicle node 42n then moves to the position P(n2) apart from the position P(o2) by the length d3 in the direction from the position P(o2) to the position P(n1).

In this way, the forward reaching phase processing in the FABRIK computing includes determination of a new position of a parent node 42 of each node 42 based on the position to which the node 42 made to correspond to each tracker 12 is to move and the current position of the parent node 42. Further, the determination is executed on condition that the length between each node 42 made to correspond to one tracker 12 and the parent node 42 of the node 42 is kept constant. The node 42 made to correspond to the tracker 12 will be referred to as "target node," hereinafter.

A backward reaching phase in the FABRIK computing will be described hereinafter with reference to FIG. 5.

First, the right clavicle node 42n moves from the position P(n2) to the position P(n3). The position P(n3) depicted in FIG. 5 is here the same position as the position P(n1) of the right clavicle node 42n at a time of starting the FABRIK computing. The right upper arm node 42o then moves to the position P(o3) apart from the position P(n3) by the length d3 in the direction from the position P(n3) to the position P(o2). The right front arm node 42p then moves to the position P(p3) apart from the position P(o3) by the length d2 in the direction from the position P(o3) to the position P(p2). The right hand node 42c then moves to the position P(c3) apart from the position P(p3) by the length d1 in the direction from the position P(p3) to the position P(c2).

The forward reaching phase and the backward reaching phase are repeatedly executed until the length between the position of the right hand node 42c and the position T1 is equal to or smaller than the predetermined threshold. It is noted that the FABRIK computing is ended when the forward reaching phase and the backward reaching phase are repeatedly executed a predetermined number of times (for example, ten times) even if the length between the position of the right hand node 42c and the position T1 is not equal to or smaller than the predetermined threshold.

In this way, the posture of the skeleton model 40 is determined by a simple algorithm in the FABRIK computing. As a result, however, joints are not bent in natural directions and the posture of the skeleton model 40 which is impossible as that of the human body is sometimes determined.

Further, in the case of determining the posture in the FABRIK computing, information regarding a rotation of each hand about an axis in the arm direction is not reflected in a rotation of each elbow about an axis in the arm direction although this information can be acquired from trackers 12b and 12c.

Further, in the FABRIK computing performed on the skeleton model 40 of the tree structure, it is necessary to execute independent forward reaching phase processing on a node group that contains a plurality of target nodes with each of the plurality of target nodes used as a starting point. Owing to this, the forward reaching phase processing sometimes causes overall postures of a plurality of nodes, for example, from the chest to the shoulders in the vicinity of junctions of the skeleton model 40 of the tree structure to get greatly distorted although the overall postures are not supposed to get greatly distorted.

As described so far, a result with low adequacy is sometimes obtained in the determination of the posture of the skeleton model 40 by using the FABRIK computing.

Taking these respects into account, the present embodiment is designed to be capable of improving the adequacy of the determination result of the posture of the skeleton model 40 by using the FABRIK computing as follows.

Functions of the entertainment apparatus 14 according to the present embodiment and processing executed in the entertainment apparatus 14 according to the present embodiment will be further described, hereinafter.

Figure 6:
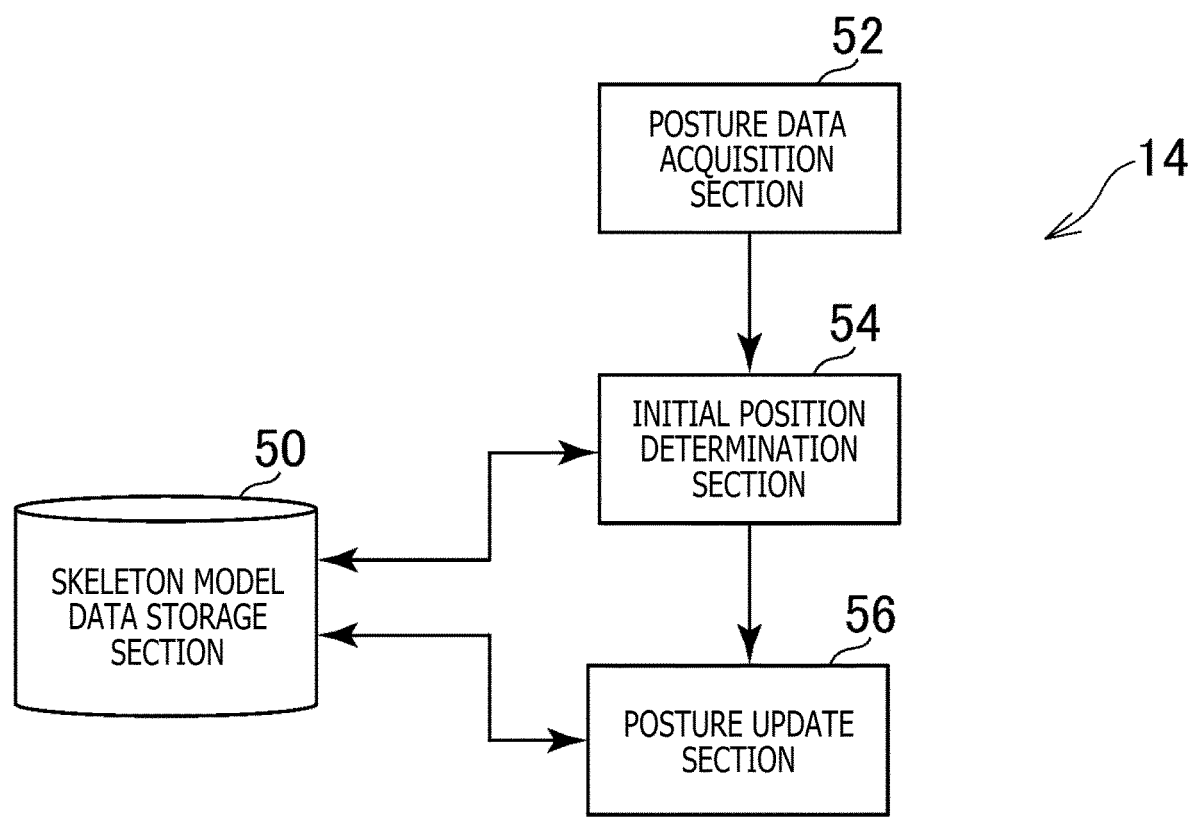
FIG. 6 is a functional block diagram depicting an example of functions implemented by the entertainment apparatus according to the embodiment of the present invention.

FIG. 6 is a functional block diagram depicting an example of functions of the entertainment apparatus 14 according to the present embodiment. It is noted that the entertainment apparatus 14 according to the present embodiment does not necessarily implement therein all functions depicted in FIG. 6 and may implement therein functions other than those depicted in FIG. 6.

As depicted in FIG. 6, the entertainment apparatus 14 according to the present embodiment functionally includes a skeleton model data storage section 50, a posture data acquisition section 52, an initial position determination section 54, and a posture update section 56.

The skeleton model data storage section 50 is implemented mainly in the storage section 32. The posture data acquisition section 52 is implemented mainly in the processor 30 and the input/output section 36. The initial position determination section 54 and the posture update section 56 are implemented mainly in the processor 30.

The functions described above may be implemented by causing the processor 30 to execute a program that is installed into the entertainment apparatus 14, which is a computer, and that includes commands corresponding to the functions described above. This program may be supplied to the entertainment apparatus 14, for example, via a computer readable information storage medium such as an optical disk, a magnetic disk, a magnetic tape, a magneto-optical disk, or a flash memory, or via the Internet.

The skeleton model data storage section 50 stores, for example, skeleton model data indicating the posture of the skeleton model 40 in the present embodiment. The skeleton model data may contain, for example, data indicating positions of the plurality of nodes 42, individually. The skeleton model data may also contain data indicating directions of the nodes 42. The data indicating the directions may be here, for example, data indicating rotation amounts in three axial directions, individually. The skeleton model data may also contain data indicating positions and directions of the bones 44. The positions and directions of the bones 44 are uniquely determined on the basis of positions of the nodes 42 on two ends of each of the bones 44.

It is also assumed in the present embodiment that the skeleton model data storage section 50 stores skeleton model data indicating a latest posture of the skeleton model 40. In addition, it is assumed that the skeleton model data storage section 50 also stores skeleton model data indicating a posture of the skeleton model 40 assuming a basic posture such as an A-pose in the initial state.

The posture data acquisition section 52 acquires, for example, posture data indicating the positions and the directions of the trackers 12a to 12e identified at a predetermined sampling rate in the present embodiment. For example, the trackers 12 may generate here, for example, the posture data indicating the positions and the directions of the trackers 12 at the predetermined sampling rate. The trackers 12 may then transmit the posture data generated by the trackers 12 to the entertainment apparatus 14 via the relay apparatus 16 according to the generation. Alternatively, the camera microphone unit 20 may generate for example, the posture data indicating the positions and the directions of the trackers 12a to 12e at the predetermined sampling rate. The camera microphone unit 20 may then transmit the posture data generated by the camera microphone unit 20 to the entertainment apparatus 14 according to the generation.

The initial position determination section 54 determines, for example, initial positions of some of the nodes 42 on the basis of the posture data acquired by the posture data acquisition section 52 in the present embodiment.

The posture update section 56 updates, for example, the posture of the skeleton model 40 in the present embodiment. The posture update section 56 updates here, for example, the skeleton model data stored in the skeleton model data storage section 50. The posture update section 56 may update the posture of the skeleton model 40 by the Forward and Backward Reaching Inverse Kinematics (FABRIK) computing on the basis of the posture data acquired by the posture data acquisition section 52 and the initial positions determined by the initial position determination section 54.

Figure 7:
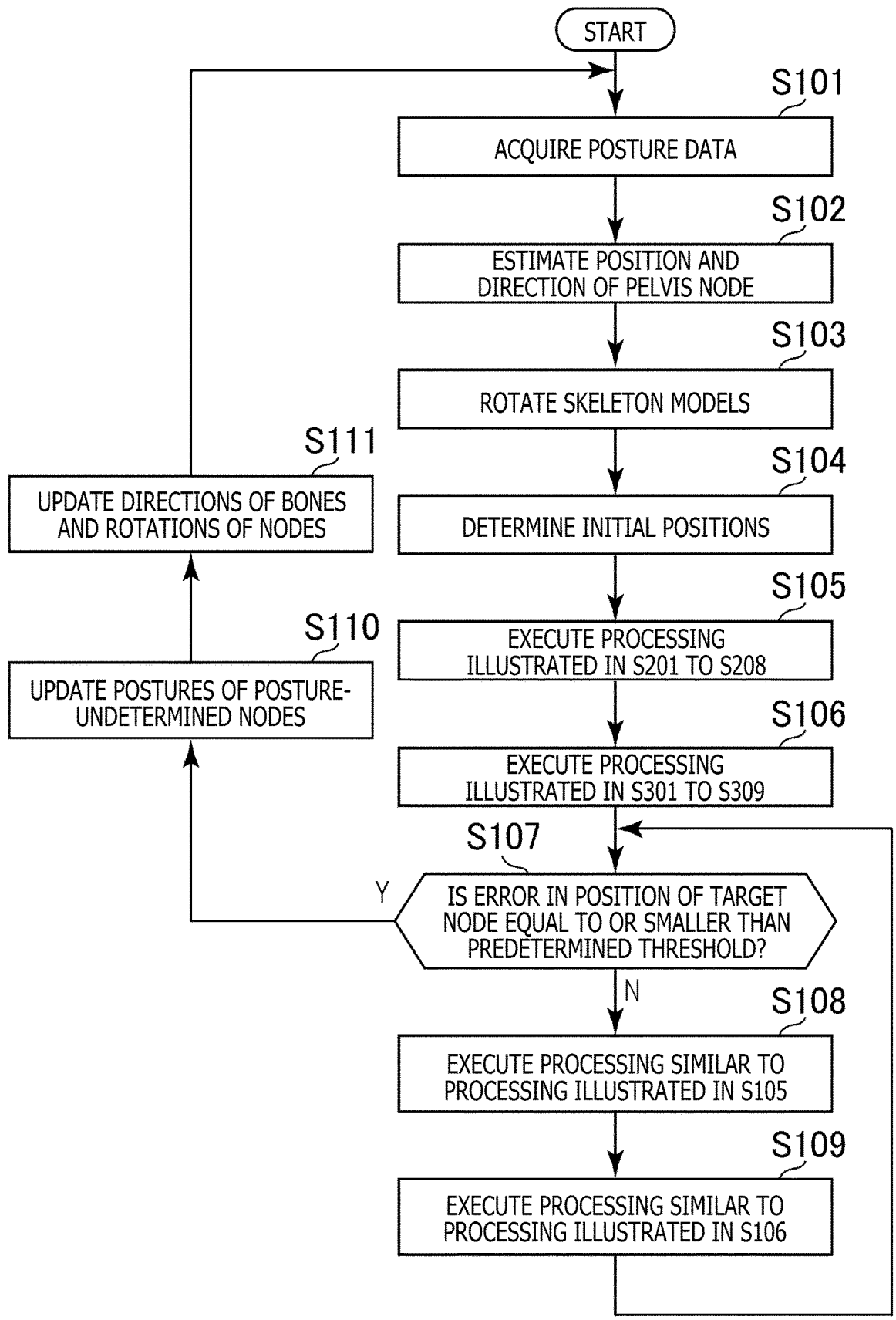
FIG. 7 is a flowchart depicting an example of a flow of processing performed by the entertainment apparatus according to the embodiment of the present invention.

An example of a flow of processing performed by the entertainment apparatus 14 according to the present embodiment will now be described with reference to a flowchart illustrated in FIG. 7.

First, the posture data acquisition section 52 acquires posture data generated by each tracker 12 and indicating the position and the direction of the tracker 12 at the latest specific timing (S101). The posture data acquisition section 52 acquires here, for example, the posture data indicating the position and the direction of each of the trackers 12 regarding each of the trackers 12a to 12e.

The posture update section 56 then estimates a position and a direction of the pelvis node 42f on the basis of the posture data acquired in the processing illustrated in S101 (S102). The posture update section 56 may estimate here, for example, a position and a direction of the third spine node 42i as an alternative to the position and the direction of the pelvis node 42f. In another alternative, the posture update section 56 may estimate, for example, the positions and the directions of the pelvis node 42f and the third spine node 42i.

The posture update section 56 then updates skeleton model data on the basis of an estimation result of the processing illustrated in S102 (S103). In the processing illustrated in S103, the posture update section 56 executes, for example, processing for rotating the latest skeleton model 40 and the skeleton model 40 in the initial state.

The initial position determination section 54 then determines initial positions of part of the nodes 42 included in the skeleton model 40 (S104).

Figure 8:
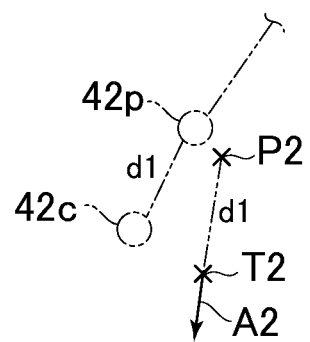
FIG. 8 is an explanatory diagram of an example of determination of an initial position of a node.

As depicted in, for example, FIG. 8, a position T2 to which the right hand node 42c that is the target node is to move and a direction A2 in which the right hand node 42c is to be directed are identified here on the basis of the position of the tracker 12c indicated by the posture data acquired in the processing illustrated in S101. A position P2 apart from the position T2 by the length d1 along the direction A2 in an opposite direction to the direction A2 is then determined as the initial position of the right front arm node 42p that is a parent node 42 of the right hand node 42c. The length d1 is here the length of the bone 44m as described above.

It is noted here that a position obtained by interpolating a current position and the position P2 of the right front arm node 42p with a predetermined weight may be determined as the initial position of the right front arm node 42p.

Further, the weight may be determined on the basis of a length, between the current position of the right hand node 42c and the position T2, made to correspond to a speed of the tracker 12c. For example, a position closer to the current position of the right front arm node 42p may be determined as the initial position of the right front arm node 42p as the length between the current position of the right hand node 42c and the position T2 is smaller. By doing so, it is possible to avoid a situation in which an elbow of a player object greatly moves in a case of, for example, player's rotating only a wrist.

Figure 9:
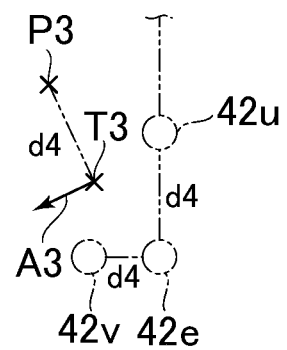
FIG. 9 is an explanatory diagram of an example of determination of an initial position of a node.

Further, as depicted in FIG. 9, a position T3 to which the right foot node 42e that is the target node is to move and a direction A3 in which the right foot node 42e is to be directed, for example, are identified on the basis of the position of the tracker 12e indicated by the posture data acquired in the processing depicted in S101. A position P3 apart from the position T3 by a length d4 in a direction rotated by a predetermined angle (for example, 90 degrees) about an axis in a transverse direction with the direction A3 set as a reference direction is then determined as an initial position of the right calf node 42u that is a parent node 42 of the right foot node 42e. The length d4 is here a length of the bone 44t.

It is noted that a position obtained by interpolating a current position of the right calf node 42u and the position P3 may be determined as the initial position of the right calf node 42u in a similar manner as that of the example described above.

Likewise, a position to which the left hand node 42b that is the target node is to move and a direction in which the left hand node 42b is to be directed, for example, are identified on the basis of the position of the tracker 12b indicated by the posture data acquired in the processing illustrated in S101. Likewise, a position to which the left foot node 42d that is the target node is to move and a direction in which the left foot node 42d is to be directed, for example, are also identified on the basis of the position of the tracker 12d indicated by the posture data acquired in the processing illustrated in S101. Likewise, initial positions of the other nodes 42 such as the left front arm node 42m and the left calf node 42r, for example, are then determined.

Figure 10:
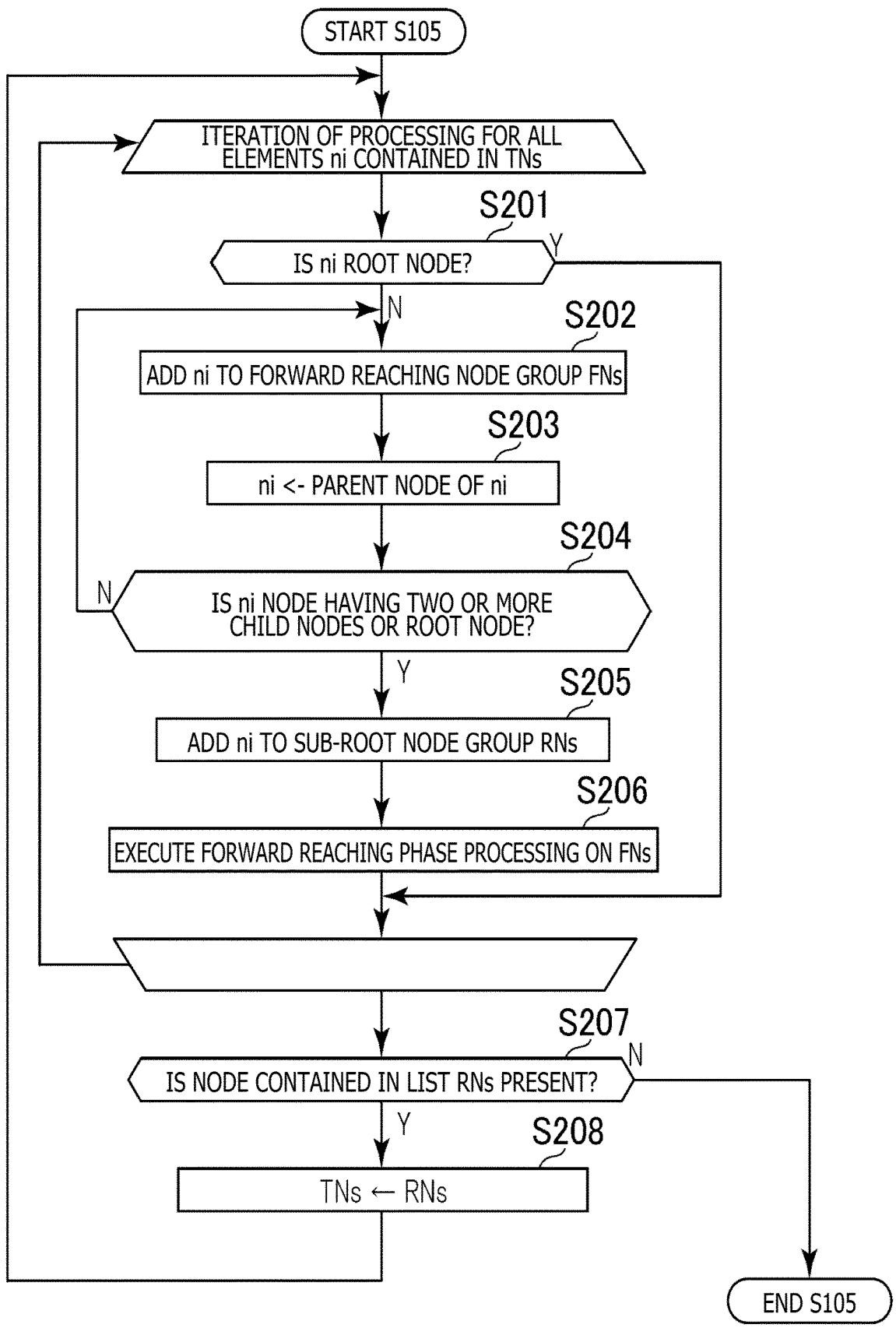
FIG. 10 is a flowchart depicting an example of a flow of processing performed by the entertainment apparatus according to the embodiment of the present invention.

The posture update section 56 then executes processing illustrated in S201 to S208 of FIG. 10 with a list of the head node 42a, the left hand node 42b, the right hand node 42c, the left foot node 42d, and the right foot node 42e as argument TNs (S105).

In the processing illustrated in S105 with the list TNs of the nodes 42 as the arguments, processing illustrated in S201 to S206 to be described hereinafter is repeatedly executed on each of all elements ni contained in the TNs.

First, the posture update section 56 confirms whether or not the ni is the root node (pelvis node 42f) (S201). In a case in which the ni is the root node (S201: Y), the posture update section 56 exits from a loop of the processing illustrated in S201 to S206.

In a case in which the ni is not the root node (S201: N), the posture update section 56 adds the ni to a list FNs representing a forward reaching node group in a current loop of the processing illustrated in S201 to S206 (S202).

The posture update section 56 then updates the ni to a parent node 42 of the ni (S203).

The posture update section 56 then confirms whether or not the ni is the node 42 having two or more child nodes 42 or the pelvis node 42f that is the root node (S204).

In a case in which the ni is neither the node 42 having two or more child nodes 42 nor the root node (S204: N), the posture update section 56 returns to the processing illustrated in S202.

In a case in which the ni is the node 42 having two or more child nodes 42 or the root node (S205: Y), the posture update section 56 adds the ni to a list RNs representing a sub-root node group (S205).

The posture update section 56 then executes forward reaching phase processing of the FABRIK described with respect to FIG. 4 on each of the nodes 42 contained in the FNs (S206).

When being completed with execution of the processing illustrated in S201 to S206 on all the elements ni contained in the TNs, the posture update section 56 confirms whether or not a node 42 contained in the list RNs is present (S207).

In a case in which the node 42 contained in the list RNs is present (S207: Y), the posture update section 56 sets the list RNs to a list TNs in a next loop (S208) and returns to the processing illustrated in S201. In this case, at a next time of executing the processing illustrated in S202, the posture update section 56 adds the ni to the new list FNs.

In a case in which it is confirmed that the node 42 contained in the list RNs is not present in the processing illustrated in S207 (S207: N), the processing illustrated in S105 is ended.

As for the skeleton model 40 depicted in FIG. 3, five lists FNs each representing the forward reaching node group are generated in the initial loop of the processing illustrated in S201 to S208 by the processing described so far. The first FNs contains, for example, the head node 42a and the neck node 42j. The second FNs contains, for example, the left hand node 42b, the left front arm node 42m, the left upper arm node 42l, and the left clavicle node 42k. The third FNs contains, for example, the right hand node 42c, the right front arm node 42p, the right upper arm node 42o, and the right clavicle node 42n. The fourth FNs contains, for example, the left foot node 42d, the left calf node 42r, and the left femoral region node 42q. The fifth FNs contains, for example, the right foot node 42e, the right calf node 42u, and the right femoral region node 42t.

In addition, the list RNs representing the sub-root node group in the initial loop of the processing illustrated in S201 to S208 contains the pelvis node 42f that is the root node and the third spine node 42i. These nodes 42 are the nodes 42 as junctions in the skeleton model 40.

Further, one list FNs representing the forward reaching node group is generated in a second loop of the processing illustrated in S201 to S208. The list FNs contains the pelvis node 42f, the first spine node 42g, the second spine node 42h, and the third spine node 42i. In addition, the list RNs representing the sub-root node group is empty in the second loop of the processing illustrated in S201 to S208.

Figure 11:
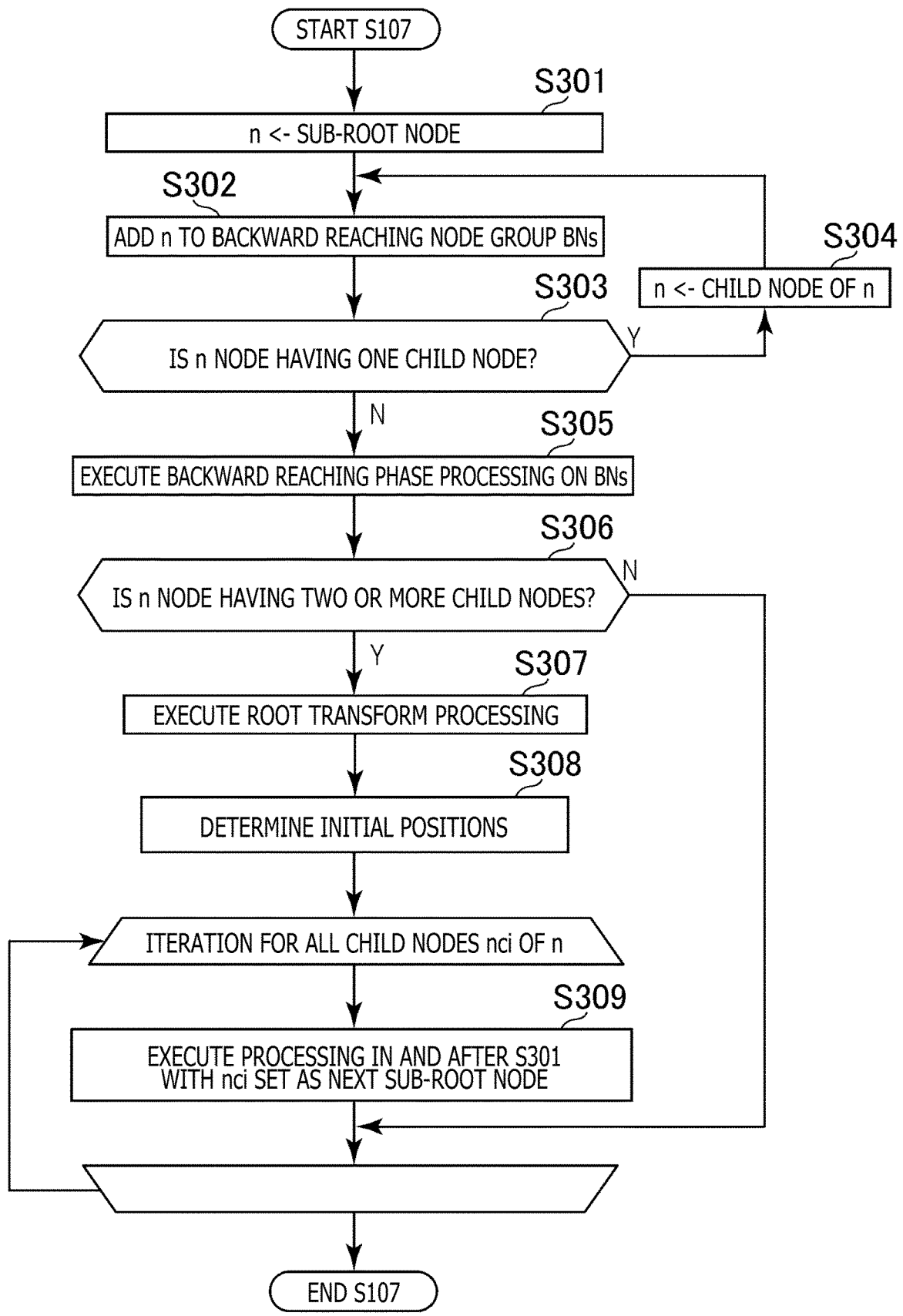
FIG. 11 is a flowchart depicting an example of a flow of processing performed by the entertainment apparatus according to the embodiment of the present invention.

When the processing illustrated in S105 is ended, the posture update section 56 executes processing illustrated in S301 to S309 of FIG. 11 (S106).

In the processing illustrated in S106, the processing illustrated in S301 to S309 is executed with all the nodes 42 (sub-root nodes) contained in the list RNs in the initial loop of the processing illustrated in S201 to S208 as arguments. In the case here in which the number of nodes 42 contained in the RNs is two as described above, the processing illustrated in S301 to S309 is executed twice. It is noted that the processing illustrated in S301 to S309 is executed on each of the nodes 42 on which the processing illustrated in S105 is executed. For that reason, the processing illustrated in S301 to S309 is executed on the assumption that the skeleton model 40 does not include the left thenar node 42s and the right thenar node 42v.

First, the posture update section 56 sets the sub-root node that is the argument to an element n (S301).

The posture update section 56 then adds the n to a list BNs representing a backward reaching node group (S302).

The posture update section 56 then confirms whether or not the n is the node 42 having one child node 42 (S303).

In a case of confirming that the n is the node 42 having one child node 42 (S303: Y), the posture update section 56 updates the n to the child node 42 of the n (S304) and returns to the processing illustrated in S302.

In a case of confirming that the n is not the node 42 having one child node 42 (S303: N), the posture update section 56 executes the backward reaching phase processing of the FABRIK described with respect to FIG. 5 on each of the nodes 42 contained in the BNs (S305). It is noted here that the posture update section 56 does not execute the backward reaching phase processing in a case in which the number of nodes 42 contained in the BNs is one.

The posture update section 56 then confirms whether or not the n is the node 42 having two or more child nodes (S306).

In a case of confirming that the n is the node 42 having two or more child nodes 42 (S306: Y), the posture update section 56 executes root transform processing (S307).

The root transform processing illustrated in S307 refers to, for example, processing for updating postures of part of the nodes 42 included in the skeleton model 40. In the case in which the n is the node 42 having two or more child nodes 42, the n is the node 42 that is the junction included in the skeleton model 40. For example, the postures of part of the nodes 42 may be updated here in such a manner that positions and directions of a plurality of nodes including the node 42 that is the junction match relative positions and relative directions in the basic posture.

For example, postures of the third spine node 42i, the left clavicle node 42k, and the right clavicle node 42n may be updated here on the basis of the third spine node 42i. For example, a rotation of the left upper arm node 42l based on the basic posture about an axis that is the bone 44c connecting the third spine node 42i to the second spine node 42h may be identified, on the basis of a position of the left upper arm node 42l. Further, for example, a rotation of the right upper arm node 42o based on the basic posture about the axis that is the bone 44c may be identified on the basis of a position of the right upper arm node 42o. The postures of the third spine node 42i, the left clavicle node 42k, and the right clavicle node 42n may be then updated by executing spherical linear interpolation by a quaternion on the basis of the two rotations identified in this way. Likewise, the postures of the pelvis node 42f, the left femoral region node 42q, and the right femoral region node 42t may also be updated on the basis of the pelvis node 42f.

The initial position determination section 54 then determines initial positions of some of the nodes 42 included in the skeleton model 40 (S308). For example, it is assumed that the postures of the third spine node 42i, the left clavicle node 42k, and the right clavicle node 42n are updated in the processing illustrated in S307. In this case, the initial positions of the right upper arm node 42o, the left upper arm node 42l, the neck node 42j, and the second spine node 42h are determined on the basis of the updated postures of these nodes 42 and the basic posture of the skeleton model 40. The initial positions of these nodes 42 may be determined here in such a manner that the positions or the directions of these nodes 42 are based on the third spine node 42i that is the sub-root node in the basic posture. It is also assumed, for example, that the postures of the pelvis node 42f, the left femoral region node 42q, and the right femoral region node 42t are updated in the processing illustrated in S307. In this case, the initial position of the first spine node 42g may be determined on the basis of the updated postures of these nodes 42 and the basic posture of the skeleton model 40. For example, the initial position of the first spine node 42g may be determined in such a manner that the position or the direction of the first spine node 42g is based on the pelvis node 42f that is the sub-root node in the basic posture.

The processing in and after S301 is recursively, repeatedly executed on each of all elements nci that are child nodes 42 of the n with each nci set as a next sub-root node (S309).

In a case in which it is confirmed that the n is not the node 42 having two or more child nodes 42 in the processing illustrated in S306 (S306: N), the processing illustrated in S309 on the sub-root node is ended. In other words, in a case in which the sub-root node is a terminal node 42 in the skeleton model 40 on which the processing illustrated in S301 to S309 is executed, the processing illustrated in S309 on the sub-root node is ended.

When the element nci on which the processing illustrated in S309 is executed is not present any more, the processing illustrated in S106 is ended.

In the processing illustrated in S106, the backward reaching phase processing is executed, for example, on the pelvis node 42f, the left femoral region node 42q, the left calf node 42r, and the left foot node 42d.

In addition, the backward reaching phase processing is executed on the pelvis node 42f, the right femoral region node 42t, the right calf node 42u, and the right foot node 42e.

Further, the backward reaching phase processing is executed on the pelvis node 42f, the first spine node 42g, the second spine node 42h, and the third spine node 42i.

Further, the backward reaching phase processing is executed on the third spine node 42i, the neck node 42j, and the head node 42a.

Further, the backward reaching phase processing is executed on the third spine node 42i, the left clavicle node 42k, the left upper arm node 42l, the left front arm node 42m, and the left hand node 42b.

Further, the backward reaching phase processing is executed on the third spine node 42i, the right clavicle node 42n, the right upper arm node 42o, the right front arm node 42p, and the right hand node 42c.

When the processing illustrated in S106 is ended, the posture update section 56 confirms whether or not an error in the positions of the target nodes is equal to or smaller than a predetermined threshold (S107). The posture update section 56 confirms here, for example, whether or not a sum of lengths between the positions of the nodes 42 and the positions to which the nodes 42 are to move and which are identified on the basis of the measurement results of the trackers 12 is equal to or smaller than the predetermined threshold.

In a case in which the error in the positions of the target nodes is not equal to or smaller than the predetermined threshold (S107: N), the posture update section 56 executes processing similar to the processing illustrated in S105 (S108). The posture update section 56 then executes processing similar to the processing illustrated in S106 (S109). The posture update section 56 then returns to the processing illustrated in S107. In the processing illustrated in S108 and S109, the lists described above may be reused.

In a case of confirming that the error in the positions of the target nodes is equal to or smaller than the predetermined threshold in the processing illustrated in S107 (S107: Y), the posture update section 56 updates postures of posture-undetermined nodes 42 (S110). It is noted that in a case in which the processing illustrated in S108 and the processing illustrated in S109 are executed a predetermined number of times, the processing illustrated in S110 may be executed even if the error in the positions of the target nodes is not equal to or smaller than the predetermined threshold.

In the processing illustrated in S110, the postures of, for example, the left thenar node 42s and the right thenar node 42v are updated. In this case, the posture of the left thenar node 42s may be updated in such a manner that a relative posture of the left thenar node 42s based on the posture of the left foot node 42d matches the relative posture in the basic posture. In addition, the posture of the right thenar node 42v may be updated in such a manner that a relative posture of the right thenar node 42v based on the posture of the right foot node 42e matches the relative posture in the basic posture.

The posture update section 56 then updates the directions of the bones 44 and the rotations of the nodes 42 (S111) and returns to the processing illustrated in S101. The posture update section 56 then executes the processing illustrated in S101 to S111 on the basis of posture data indicating the positions and the directions of the trackers 12 at newly acquired latest specific timing. In this way, the processing illustrated in S101 to S111 is repeatedly executed.

For example, the directions of the bones 44 can uniquely be identified here on the basis of the positions of the nodes 42 on both ends of each of the bones 44. However, it is impossible to identify the rotation about an axis that is each bone 44 from the positions of the nodes 42 on both ends of the bone 44.

Figure 12:
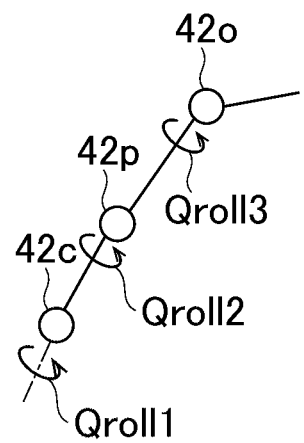
FIG. 12 is an explanatory diagram of an example of determination of a rotation of a node.

In the processing illustrated in S111, therefore, the posture update section 56 separates the rotation of each of the trackers 12b and 12c indicated by the posture data into, for example, a component of a bend of the wrist with respect to the arm, a component of a rotation of the arm with respect to the basic posture, and a component of a rotation about an axis in the direction of the arm. In FIG. 12, a component of a rotation of the right hand node 42c about an axis in a direction along the bone 44m is denoted as Qroll1.

The posture update section 56 then determines the rotations of the upper arm and the front arm on the basis of the rotation about the axis in the direction of the arm. The posture update section 56 determines here, for example, a component of a rotation of the right hand node 42c about the axis that is the bone 44m, as a rotation Qroll2 of the right front arm node 42p about the axis in the direction of the arm and a rotation Qroll3 of the right upper arm node 42o about the axis in the direction of the arm. Likewise, the posture update section 56 determines a component of a rotation of the left hand node 42b about an axis that is the bone 44i, as rotations of the left front arm node 42m and the left upper arm node 42l about an axis in the direction of the arm.

For example, an upper limit of 60 degrees or the like may be set in advance to a difference between the Qroll1 and the Qroll2 and a difference between the Qroll2 and the Qroll3. Further, a value obtained by multiplying a value of the Qroll1 by a predetermined coefficient equal to or smaller than 1 may be set as a value of the Qroll2. Further, a value obtained by multiplying the value of the Qroll2 by a predetermined coefficient equal to or smaller than 1 may be set as a value of the Qroll3.

As described so far, in the present embodiment, in the processing illustrated in S101, the posture data acquisition section 52 acquires, for example, the posture data indicating the posture of each target node included in the skeleton model 40 of the tree structure. In the processing illustrated in S104, the initial position determination section 54 then determines the position to which the target node is to move on the basis of the posture data. In the processing illustrated in S104, the initial position determination section 54 then determines the initial position of the parent node 42 of the target node in the FABRIK computing on the basis of the position to which the target node is to move and a given posture of the skeleton model 40. Further, in the processing illustrated in S308, the initial position determination section 54 determines the initial positions of some of the nodes 42 on the basis of the position to which the target node is to move and the given posture of the skeleton model 40.

In the example described above, for example, the position apart from the position T2 to which the right hand node 42c is to move by the length d1 in the opposite direction to the direction A2 along the direction A2 corresponds to the given posture for the initial position of the right front arm node 42p. Further, for example, the position apart from the position T3 by the length d4 in the direction rotated at the predetermined angle (for example, 90 degrees) about the axis in the transverse direction with the direction A3 set as the reference direction corresponds to the given posture for the initial position of the right calf node 42u.

Further, a given position and a given direction based on the root node in the basic posture correspond to the given posture for the initial positions of the right upper arm node 42o, the left upper arm node 42l, the neck node 42j, the second spine node 42h, and the first spine node 42g.

Further, in the processing illustrated in S105 to S111, the posture update section 56 executes the FABRIK computing including determination of a new position of the parent node 42 of each target node on the basis of the position to which the target node is to move and the initial position of the parent node 42. As a result, the posture of the skeleton model 40 is updated.

In this way, according to the present embodiment, a probability decreases in the determination of the posture by using the FABRIK computing that joints are not bent in natural directions and the posture of the skeleton model 40 which is impossible as that of the human body and lacks adequacy is sometimes determined. As a result, it is possible to improve adequacy of a determination result of the posture of the skeleton model 40.

Further, in the present embodiment, in the processing illustrated in S101, the posture data acquisition section 52 acquires, for example, the posture data indicating the posture of each target node included in the skeleton model 40 of the tree structure. In the processing illustrated in S102 to S109, the posture update section 56 then updates the posture of the skeleton model 40 by executing the FABRIK computing including the determination of the new position of the parent node 42 of the target node. In the processing illustrated in S111, the posture update section 56 then identifies the rotation of the target node about an axis that is the bone 44 connecting the target node to the parent node 42 of the target node on the basis of the posture data. In the processing illustrated in S111, the posture update section 56 then determines the rotation of the parent node 42 of the target node on the basis of the rotation of the target node.

In this way, according to the present embodiment, it is possible to perform the determination of the rotation about an axis in the arm direction based on the measurement results of each tracker 12. As a result, it is possible to improve the adequacy of the determination result of the posture of the skeleton model 40.

Further, in the present embodiment, in the processing illustrated in S101, the posture data acquisition section 52 acquires, for example, posture data indicating a posture of a first target node included in the skeleton model 40 of the tree structure and postures of a plurality of nodes 42 including a second target node.

In the processing illustrated in S207, the posture update section 56 then updates postures of a first node group containing nodes including the first target node and connected to one another by the forward reaching phase processing in the FABRIK computing on the basis of the posture data. In addition, in the same processing illustrated in S207, the posture update section 56 updates postures of a second node group containing nodes including the second target node and connected to one another by the forward reaching phase processing in the FABRIK computing.

In the processing illustrated in S307, the posture update section 56 then updates the postures of the plurality of nodes 42 after updating the first node group and the second node group. The plurality of nodes 42 include, for example, here the nodes 42 included in the first node group and closest to the junctions included in the skeleton model 40 and the nodes 42 included in the second node group and closest to the junctions included in the skeleton model 40.

Further, in the processing illustrated in S304, the posture update section 56 updates the posture of the skeleton model 40 by the backward reaching phase processing in the FABRIK computing.

In this way, in the present embodiment, it is possible to prevent overall postures of a plurality of nodes in the vicinity of junctions of the skeleton model 40 of the tree structure, for example, from the chest to the shoulders from getting greatly distorted although the overall postures are not supposed to get greatly distorted. As a result, it is possible to improve the adequacy of the determination result of the posture of the skeleton model 40.

Further, in the processing illustrated in S102 of the present embodiment, the posture update section 46 may estimate a pivoting foot on the basis of the posture data acquired in the processing illustrated in S101.

In the following description, coordinate values on a horizontal surface will be referred to as "X and Y coordinate values" and a coordinate value in a height direction will be referred to as a "Z coordinate value" for each position indicated by the posture data. It is noted that the Z coordinate value is assumed to be greater as the position is higher.

For example, the posture update section 46 may compare a Z coordinate value of the tracker 12d corresponding to the left foot and a Z coordinate value of the tracker 12e corresponding to the right foot indicated by the posture data acquired in the processing illustrated in S101 with each other.

The posture update section 46 may then estimate the foot located at a lower position, that is, the foot corresponding to the smaller Z coordinate value as a pivoting foot in a case in which a difference between the Z coordinate values is greater than a predetermined value. The posture update section 56 may estimate, for example, the left foot as the pivoting foot in a case in which the difference between the Z coordinate values is greater than the predetermined value and the Z coordinate value of the tracker 12d is smaller than the Z coordinate value of the tracker 12e. Conversely, the posture update section 56 may estimate the right foot as the pivoting foot in a case in which the difference between the Z coordinate values is greater than the predetermined value and the Z coordinate value of the tracker 12e is smaller than the Z coordinate value of the tracker 12d.

The posture update section 46 may determine the initial position of the pelvis node 42f (lumbar node) in the FABRIK computing on the basis of the position of the pivoting foot.

The posture update section 46 may determine, for example, the same X and Y coordinate values as the X and Y coordinate values of the pivoting foot in the processing illustrated in S102 as X and Y coordinate values of the initial position of the pelvis node 42f in the FABRIK computing.

Further, in a case, for example, in which the difference between the Z coordinate values is smaller than the predetermined value, the posture update section 46 may estimate neither of the feet as the pivoting foot. In this case, the posture update section 46 may identify, for example, X and Y coordinate values of a position closest to a vertical line passing through the position of the tracker 12a indicated by the posture data acquired in the processing illustrated in S101 among positions on an ellipse passing through the positions of the trackers 12d and 12e. The posture update section 46 may then determine the identified X and Y coordinate values as the X and Y coordinate values of the initial position of the pelvis node 42f in the FABRIK computing in the processing illustrated in S102. The ellipse may be here an ellipse a major axis length of which is equal to a length between the positions of the trackers 12d and 12e and a short axis length of which is equal to a predetermined length.

Further, the posture update section 46 may determine X and Y coordinate values obtained by linearly interpolating the same X and Y coordinate values as those of the pivoting foot and the X and Y coordinate values of the position described above on the ellipse passing through the positions of the trackers 12d and 12e as the X and Y coordinate values of the initial position of the pelvis node 42f.

A weight in the linear interpolation may be determined on the basis of, for example, the difference between the Z coordinate value of the tracker 12d and the Z coordinate value of the tracker 12e. The posture update section 46 may determine, for example, the X and Y coordinate values closer to the X and Y coordinate values of the position on the ellipse described above as the X and Y coordinate values of the initial position of the pelvis node 42f as the difference between the Z coordinate values is smaller. The posture update section 46 may then determine the X and Y coordinate values closer to the same X and Y coordinate values as those of the pivoting foot as the X and Y coordinate values of the initial position of the pelvis node 42f as the difference between is greater.

Further, the posture update section 46 may correct the X and Y coordinate values of the initial position of the pelvis node 42f determined as described above on the basis of the position of the tracker 12a indicated by the posture data acquired in the processing illustrated in S101. The posture update section 46 may correct, for example, the X and Y coordinate values of the initial position of the pelvis node 42f in such a manner that the initial position of the pelvis node 42f moves along the horizontal surface in an opposite direction to a direction from the position of the pivoting foot or a position of a center of the two feet to the direction of the tracker 12a. The posture update section 46 may correct, for example, the X and Y coordinate values of the initial position of the pelvis node 42f in such a manner that the initial position of the pelvis node 42f moves backward in a case in which the position of the tracker 12a is located forward of the position of the pivoting foot or the position of the center of the two feet. Further, the posture update section 46 may correct, for example, the X and Y coordinate values of the initial position of the pelvis node 42f in such a manner that the initial position of the pelvis node 42f moves forward in a case in which the position of the tracker 12a is located backward of the position of the pivoting foot or the position of the center of the two feet.

The posture update section 46 may then determine initial positions of the bones 44e, 44d, 44c, 44b, and 44a and the Z coordinate value of the initial position of the pelvis node 42f in the FABRIK computing on the basis of the position and the direction of the tracker 12a.

Further, in the present embodiment, the posture update section 46 may estimate whether the user is in a seated posture or a standing posture by using a learned machine learning model as follows. In a case of estimating that the user is in the standing posture, the posture update section 46 may then perform pivoting foot estimation processing and determination of the initial position of the pelvis node 42f (lumbar node) in the FABRIK computing based on an estimation result of the pivoting foot.

Figure 13:
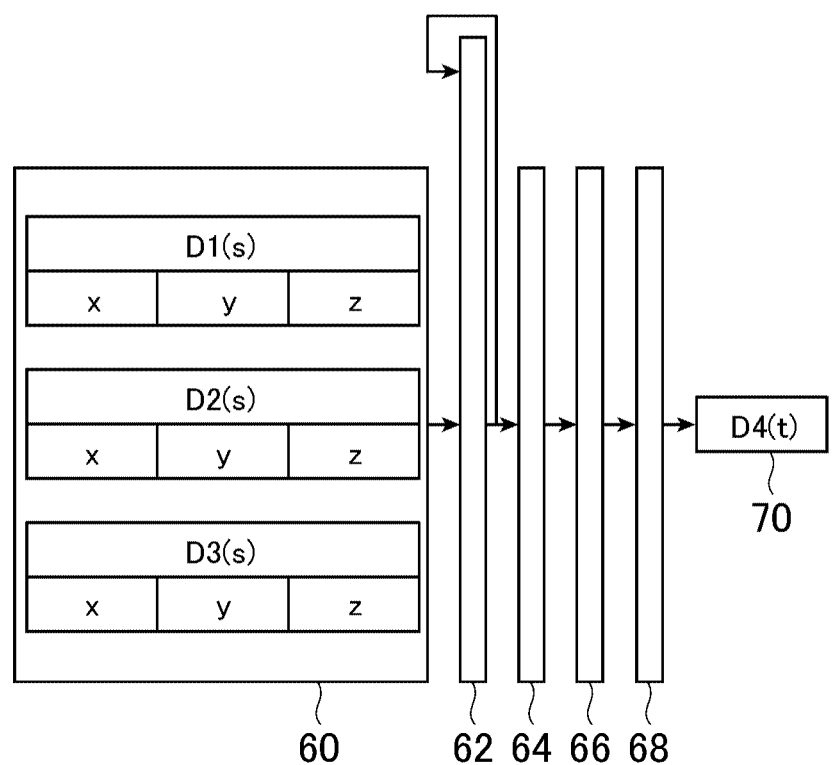
FIG. 13 is a diagram depicting learning of a machine learning model used in estimation of whether a user is in a seated posture or a standing posture.

FIG. 13 is a diagram depicting an example of learning of a machine learning model used in estimation of whether the user is in a seated posture or a standing posture. As depicted in FIG. 13, the machine learning model used in the estimation of whether the user is in the seated posture or the standing posture includes an input layer 60, an intermediate block 62, a first intermediate layer 64, a second intermediate layer 66, and an output layer 68.

In the present embodiment, in learning of the machine learning model depicted in FIG. 13, learning data containing, for example, a plurality of pieces of region data made to correspond to different timing, individually and indicating a direction of the head, a position of the head based on a position of the right foot, and a position of the head based on a position of the left foot, all of which are offset by a rotation of the lumbar (the pelvis node 42f) (based on the rotation of the lumbar), at the corresponding timing is acquired.

On the basis of, for example, sensing data output from each of the trackers 12 attached to the head, the right foot, the left foot, and the lumbar when the user having the trackers 12 attached thereto makes various motions in the seated posture, a series of pieces of region data corresponding to the seated posture may be generated. Alternatively, on the basis of, for example, an image sequence of the user making various motions in the seated posture captured from an external camera, a series of pieces of region data corresponding to the seated posture may be generated. In another alternative, a series of pieces of region data corresponding to the seated posture may be generated on the basis of an operation by an operator viewing such an image sequence.

Leaning data containing, for example, the series of pieces of region data corresponding to the seated posture described above and supervisory data having a value set to 1 may be then generated.

Further, on the basis of, for example, the sensing data output from the trackers 12 attached to the head, the right foot, the left foot, and the lumbar when the user having the trackers 12 attached thereto makes various motions in the standing posture, a series of pieces of region data corresponding to the standing posture may be generated. Alternatively, on the basis of, for example, an image sequence containing t frames of the user making various motions in the standing posture captured from the external camera, a series of pieces of region data corresponding to the standing posture may be generated. In another alternative, a series of pieces of region data corresponding to the standing posture may be generated on the basis of an operation by the operator viewing such an image sequence.

Learning data containing, for example, the series of pieces of region data corresponding to the standing posture described above and supervisory data having a value set to 0 may be then generated.

The pieces of region data contained in the learning data are sequentially input to the input layer 60 in ascending order by corresponding timing. It is assumed here that each region data contains, for example, head direction data D1 indicating a direction of the head offset by the rotation of the lumbar, right-foot-based head position data D2 indicating a position of the head based on a position of the right foot and offset by the rotation of the lumbar, and left-foot-based head position data D3 indicating a position of the head based on a position of the left foot and offset by the rotation of the lumbar.

For example, the head direction data at the corresponding timing that is s-th oldest is expressed as $D1(s)$ here. Further, the right-foot-based head position data at the corresponding timing that is the s-th oldest is expressed as $D2(s)$. Further, the left-foot-based head position data at the corresponding timing that is the s-th oldest is expressed as $D3(s)$. A value s is here an integer equal to or greater than 1 and equal to or smaller than t.

Further, in the present embodiment, as depicted in FIG. 13, the head direction data $D1(s)$ contains three elements that are x, y, and z. The three elements correspond to an x coordinate value, a y coordinate value, and a z coordinate value, individually of a vector representing the direction of the head offset by the rotation of the chest. The vector representing the direction of the head offset by the rotation of the chest may be, for example, a unit vector representing the direction of the head (head node 42a) (for example, a line-of-sight direction of the head) offset by the rotation of the chest. It is noted that the vector representing the direction of the head offset by the rotation of the chest may be a vector representing a position of the head (head node 42a) based on a position of the neck (neck node 42j). In this case, the region data contained in the learning data may be generated on the basis of sensing data output from the trackers 12 attached to the head, the right foot, the left foot, the lumbar, and the neck, individually when the user having the trackers 12 attached thereto makes various motions.

Further, in the present embodiment, as depicted in FIG. 13, the right-foot-based head position data $D2(s)$ contains three elements that are x, y, and z. The three elements correspond to an x coordinate value, a y coordinate value, and a z coordinate value, individually of the position of the head based on the position of the right foot and offset by the rotation of the lumbar.

Further, in the present embodiment, as depicted in FIG. 13, the left-foot-based head position data $D3(s)$ contains three elements that are x, y, and z. The three elements correspond to an x coordinate value, a y coordinate value, and a z coordinate value, individually of the position of the head based on the position of the left foot and offset by the rotation of the lumbar.

In the present embodiment, the pieces of region data each containing nine (3×3) elements are input to the input layer 60.

Input data obtained by connecting the region data input to the input layer 60 with an output from the intermediate block 62 according to an immediately preceding input is then input to the intermediate block 62. The intermediate block 62 is, for example, an RNN (Recurrent Neural Network) (LSTM (Long short-term memory) block) into which an LSTM is implemented.

The output from the intermediate block 62 is here data indicating a feature of a time-series transition of the position, the posture, or a motion regarding any of the regions of the body regarding which the region data indicates the position, the posture, or the motion. The data output from the intermediate block 62 will be referred to as "feature data," hereinafter. For example, state variables of the LSTM correspond to the feature data.

It is assumed here that the input data containing, for example, the region data made to correspond to certain timing and the feature data indicating the feature of the time-series transition described above at timing preceding the certain timing is input to the intermediate block 62. In this case, the intermediate block 62 outputs the feature data indicating the feature of the time-series transition until the certain timing. It is assumed that the input data containing, for example, the s-th region data and the feature data indicating the feature of the time-series transition described above until the timing corresponding to the (s−1)-th region data is input to the intermediate block 62. In this case, the intermediate block 62 outputs the feature data indicating the feature of the time-series transition until the timing corresponding to the s-th region data. The feature data indicating the feature of the time-series transition described above until the timing corresponding to the s-th region data will be referred to as "s-th feature data," hereinafter.

t-th feature data that is an output from the intermediate block 62 with respect to an input of the input data containing the last region data (t-th region data) is then input to the first intermediate layer 64. The output from the first intermediate layer 64 is then input to the second intermediate layer 66. Each of the first intermediate layer 64 and the second intermediate layer 66 is, for example, a fully-connected layer using a rectified linear function (ReLU) as an activation function.

The output from the second intermediate layer 66 is then input to the output layer 68. The output layer 68 is, for example, a layer using a linear function as an activation function. Seating probability data D4(*t*) corresponding to an estimation result of whether the user is in the seated posture or the standing posture at the latest timing (t-th timing) is then finally output from the output layer 68 as an output 70. The seating probability data is data expressed by a real number, for example, equal to or greater than 0 and equal to or smaller than 1. A probability of the user in the seated posture is higher as a value of the seating probability data is greater, and the probability of the user in the seated posture is lower as the value of the seating probability data is smaller.

In the present embodiment, learning of the intermediate block 62, the first intermediate layer 64, the second intermediate layer 66, and the output layer 68 is then executed on the basis of, for example, the seating probability data D4(*t*) indicating the estimation result. A difference between, for example, the supervisory data contained in the learning data that contains the series of region data described above and the seating probability data D4(*t*) indicating the estimation result may be identified here. Supervised learning for updating parameter values of the intermediate block 62, the first intermediate layer 64, the second intermediate layer 66, and the output layer 68 may be then executed on the basis of the identified difference.

In the present embodiment, learning is performed by, for example, the learning data containing t pieces of region data from the first region data to the t-th region data. Learning may be performed here by, for example, the learning data containing the t pieces of region data from the first region data to the t-th region data and the supervisory data made to correspond to the t pieces of region data. The estimation of whether the user in the seated posture or the standing posture is then executed by using the learned machine learning model completed with the learning by, for example, a plurality of pieces of different learning data corresponding to the seated posture and a plurality of pieces of different learning data corresponding to the standing posture.

Figure 14:
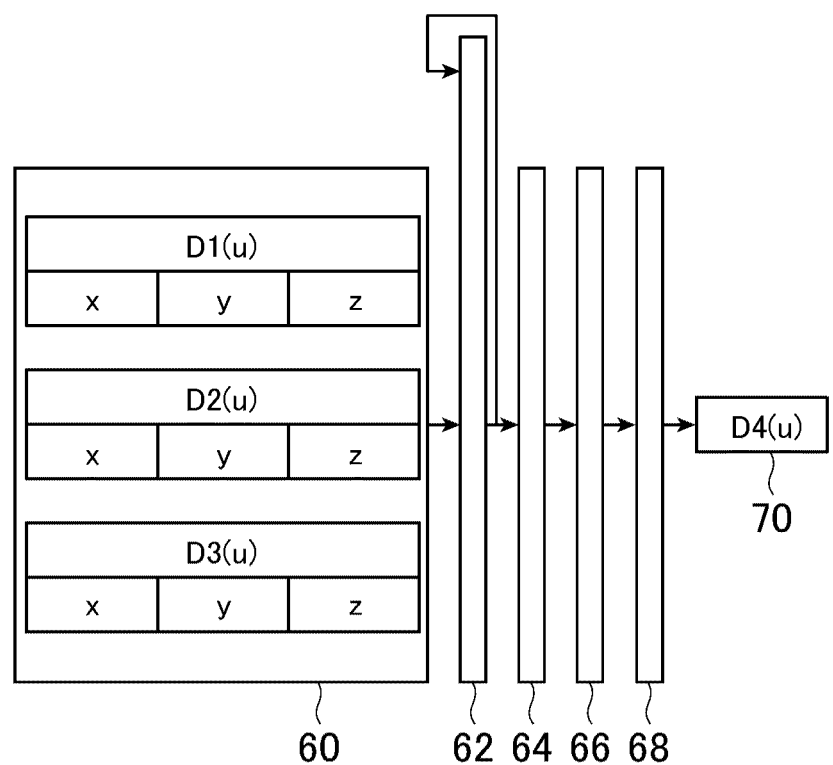
FIG. 14 is a diagram depicting an example of the estimation of whether a user is in the seated posture or the standing posture by using the learned machine learning model depicted in FIG. 13.

FIG. 14 is a diagram depicting an example of estimation of whether the user is in the seated posture or the standing posture by using the learned machine learning model.

As described above, in the present embodiment, it is assumed, for example, that the position and the direction of each of the trackers 12*a* to 12*e* are identified at the predetermined sampling rate. It is also assumed that data indicating the position and the direction of each tracker 12 is transmitted to the entertainment apparatus 14 according to identification of the position and the direction of the tracker 12.

It is then assumed that the region data described above is generated on the basis of the data indicating the position and the direction of each tracker 12 transmitted in this way. In this way, in the present embodiment, the region data is, for example, repeatedly generated.

As described above, it is assumed here that each region data contains the head direction data D1 indicating the direction of the head offset by the rotation of the lumbar, the right-foot-based head position data D2 indicating the position of the head based on the position of the right foot and offset by the rotation of the lumbar, and the left-foot-based head position data D3 indicating the position of the head based on the position of the left foot and offset by the rotation of the lumbar. It is noted that in a case in which the head direction data D1 is the vector representing the position of the head (head node 42*a*) based on the position of the neck (neck node 42*j*), the head direction data D1 may be generated on the basis of latest positions of the neck node 42*j* and the head node 42*a*.

In the present embodiment, the latest region data (last generated region data), for example, is input to the input layer 60. In FIG. 14, the head direction data contained in the latest region data is expressed as D1(*u*). Further, the right-foot-based head position data contained in the latest region data is expressed as D2(*u*). Further, the left-foot-based head position data contained in the latest region data is expressed as D3(*u*).

As described above, the head direction data D1(*u*) contains three elements that are x, y, and z. Further, the right-foot-based head position data D2(*u*) contains three elements that are x, y, and z. Further, the left-foot-based head position data D3(*u*) contains three elements that are x, y, and z.

The input data obtained by connecting the region data input to the input layer 60 and containing the nine (3×3) elements with the feature data that is the output from the intermediate block 62 according to the immediately preceding input is then input to the intermediate block 62.

The feature data that is the output from the intermediate block 62 is then input to the first intermediate layer 64. The output from the first intermediate layer 64 is then input to the second intermediate layer 66.

The output from the second intermediate layer 66 is then input to the output layer 68. Seating probability data D4(*u*) corresponding to an estimation result of whether the user is in the seated posture or the standing posture at the timing is then finally output from the output layer 68 as the output 70.

In a case in which the value of the seating probability data D4(*u*) is, for example, equal to or greater than 0.5, the user may be estimated to be in the seated posture; otherwise, the user may be estimated to be in the standing posture.

In the case of estimating that the user is in the standing posture, pivoting foot estimation processing and determination of the initial position of the pelvis node 42*f* based on the estimation result of the pivoting foot may then be performed as described above.

It is noted that it is not always necessary to estimate whether the user is in the seated posture or the standing posture by using the machine learning model. For example, whether the user is in the seated posture or the standing posture may be estimated by using a given created logic.

Further, relative values based on a body size, that is, values each obtained by dividing the coordinate values of the position of the head based on each foot position by the body size may be used as a value of the right-foot-based head position data D2 and a value of the left-foot-based head position D3.

The body size may be here input by the user in advance, and may be estimated sequentially on the basis of the positions of the trackers 12 whenever the estimation of whether the user is in the seated posture or the standing posture is performed, for example, in the following manner.

Figure 15:
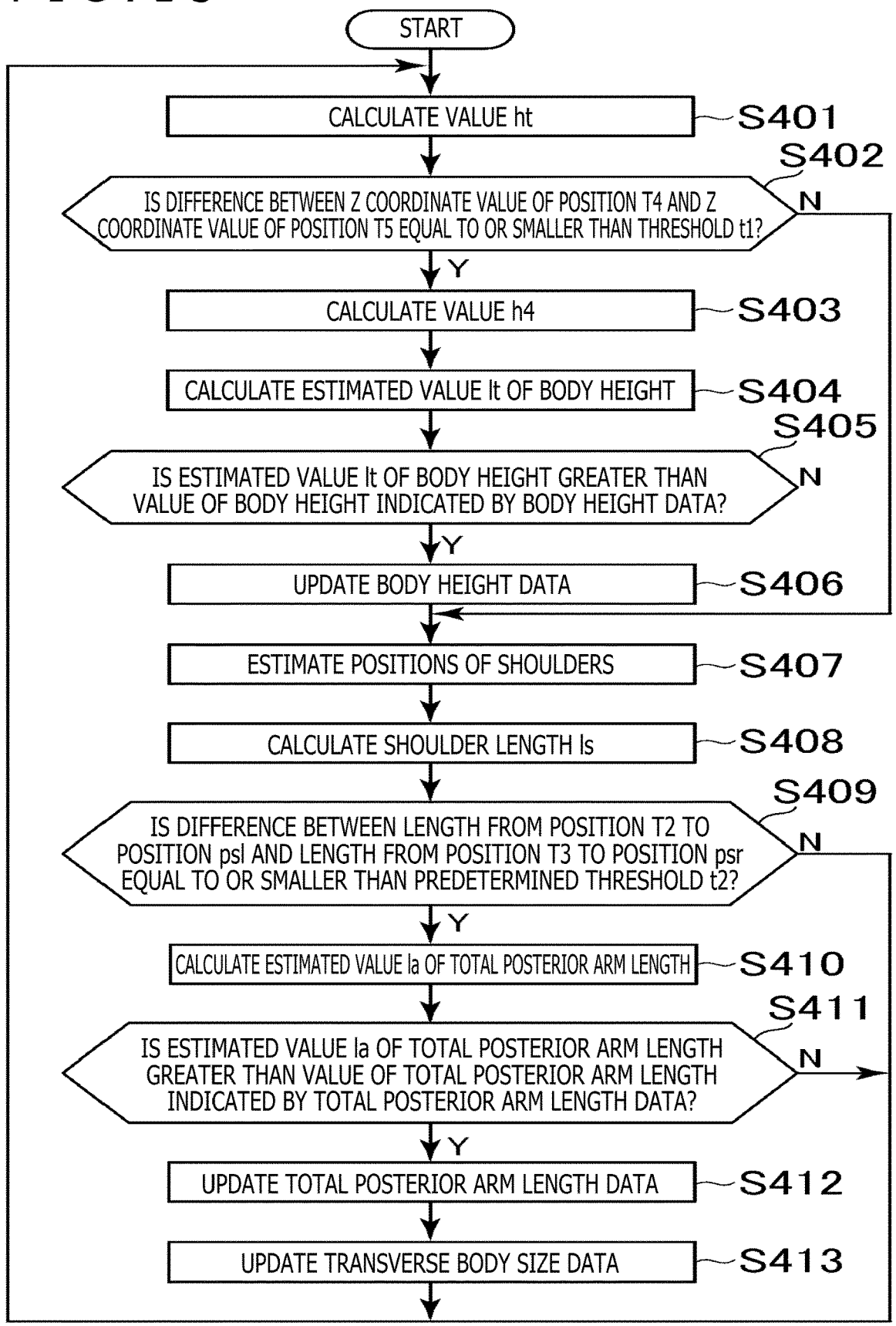
FIG. 15 is a flowchart depicting an example of a flow of processing performed by the entertainment apparatus according to the embodiment of the present invention.
Figure 16:
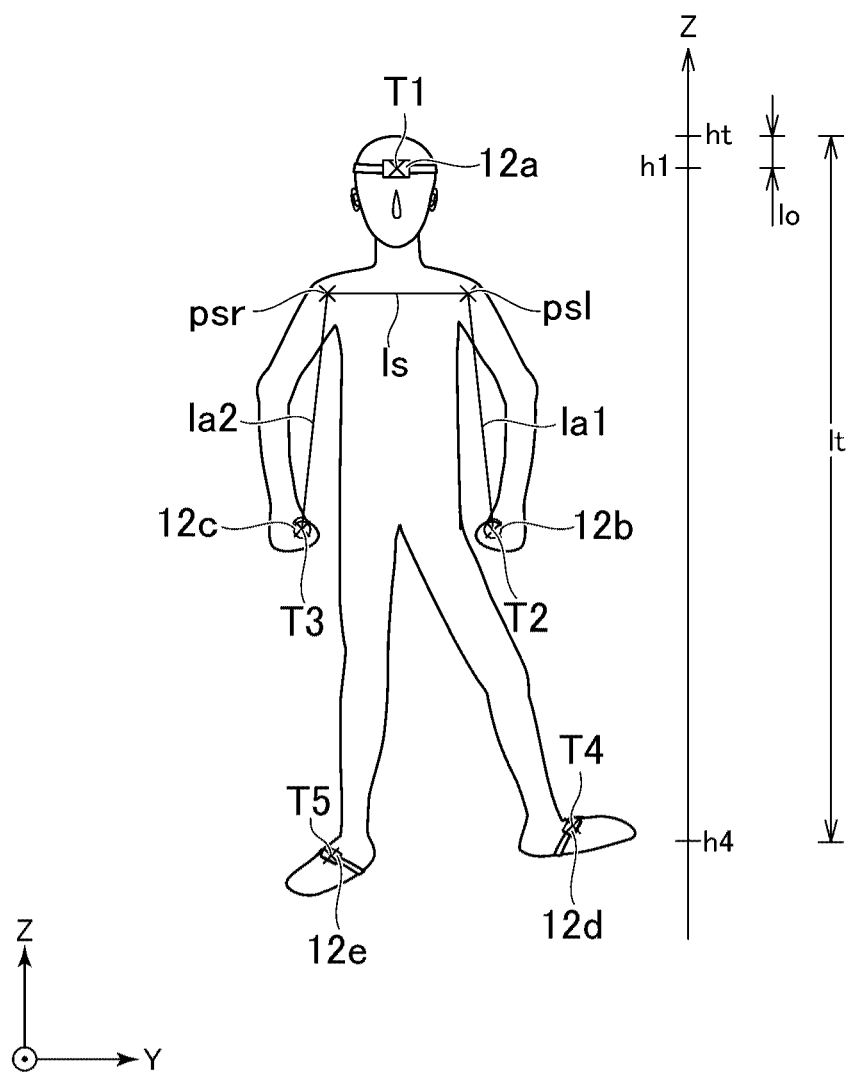
FIG. 16 is a schematic diagram depicting an example of a user's game playing state.

An example of a flow of body size estimation processing performed by the entertainment apparatus 14 according to the present embodiment will be described here with reference to a flowchart exemplarily depicted in FIG. 15 and a schematic diagram depicted in FIG. 16. FIG. 16 is a schematic diagram depicting an example of a user's game playing state. In the present processing example, the following processing illustrated in S401 to S413 is repeatedly executed at a predetermined sampling rate. The processing depicted in the present processing example may be executed just before execution of, for example, the pivoting foot estimation processing described above. It is also assumed that a user's longitudinal direction is an X-axis direction, a user's transverse direction is a Y-axis direction, and a height direction is a Z-axis direction.

In addition, in the following description, positions of the trackers 12a, 12b, 12c, 12d, and 12e indicated by the posture data acquired in the processing illustrated in S101 are expressed as T1, T2, T3, T4, and T5, respectively, as depicted in FIG. 16.

Further, it is assumed in the following description that body size data indicating a body size of the user is stored in the skeleton model data storage section 50. A predetermined value may be set here as, for example, an initial value of the body size data. Alternatively, a value according to a user's age may be set as the initial value of the body size data. Since the body size data is updated so that the body size indicated by the body size data gradually grows as described later, it is desirable to set a value slightly smaller than a value indicating a general body size of the user as the initial value of the body size data.

It is noted that the skeleton model data storage section 50 may store body height data indicating a body height of the user. In addition, the skeleton model data storage section 50 may store total posterior arm length data indicating a length of a total posterior arm length. Further, the skeleton model data storage section 50 may store transverse body size data indicating a body size of the user in the transverse direction.

First, the posture update section 56 calculates a value obtained by adding a predetermined offset value lo to a Z coordinate value h1 of the position T1 as a Z coordinate value ht of a vertex of the head (S401).

The posture update section 56 then confirms whether or not a difference between a Z coordinate value of the position T4 and a Z coordinate value of the position T5 is equal to or smaller than a predetermined threshold t1 (S402).

In a case of confirming that the difference between the Z coordinate value of the position T4 and the Z coordinate value of the position T5 is equal to or smaller than the threshold t1 (S402: Y), the posture update section 56 calculates a Z coordinate value h4 that is an average value of the Z coordinate value of the position T4 and the Z coordinate value of the position T5 (S403).

The posture update section 56 then calculates a difference between the Z coordinate value ht of the vertex of the head calculated in the processing illustrated in S401 and the Z coordinate value h4 calculated in the processing illustrated in S403 as an estimated value lt of the body height (S404).

The posture update section 56 then confirms whether or not the estimated value lt of the body size calculated in the processing illustrated in S404 is greater than a value of the body height indicated by body height data stored in the skeleton model data storage section 50 (S405).

It is assumed to be confirmed that the value lt is greater than the value of the body height indicated by the body height data stored in the skeleton model data storage section 50 (S405: Y). In this case, the posture update section 56 updates the body height data stored in the skeleton model data storage section 50 so that the body height data indicates the estimated value lt of the body size calculated in the processing illustrated in S404 (S406).

The posture update section 56 then estimates positions of shoulders of the user (S407). The posture update section 56 may estimate here, for example, a value indicating a position psr of the right shoulder by adding a predetermined offset value psro to a value indicating the position T1. In addition, the posture update section 56 may estimate a value indicating a position psl of the left shoulder by adding another predetermined offset value pslo to the value indicating the position T1. It is noted that the processing illustrated in S407 is executed even in a case in which it is confirmed that the difference between the Z coordinate value of the position T4 and the Z coordinate value of the position T5 is not equal to or smaller than the threshold t1 in the processing illustrated in S403 (S402: N). In this case, the processing illustrated in S403 to S406 is skipped since there is a high probability that the value indicating the position T4 and the value indicating the position T5 are abnormal values based on an error. Further, the processing illustrated in S407 is executed even in a case in which it is confirmed that the value lt is not greater than the value of the body height indicated by the body height data stored in the skeleton model data storage section 50 in the processing illustrated in S405 (S405: N).

The posture update section 56 then calculates a length between the position psr of the right shoulder and the position psl of the left shoulder estimated in the processing illustrated in S407 as a shoulder length is (S408).

The posture update section 56 then confirms whether or not a difference between a length from the position T2 to the position psl and a length from the position T3 to the position psr is equal to or smaller than a predetermined threshold t2 (S409).

It is assumed to be confirmed that the difference between a length la1 from the position T2 to the position psl and a length la2 from the position T3 to the position psr is equal to or smaller than the predetermined threshold t2 (S409: Y). In this case, the posture update section 56 calculates an average value between a value indicating the length la1 from the position T2 to the position psr and a value indicating the length la2 from the position T3 to the position psl as an estimated value la of a total posterior arm length (S410).

The posture update section 56 then confirms whether or not the estimated value la calculated in the processing illustrated in S410 is greater than a value of the total posterior arm length indicated by total posterior arm length data stored in the skeleton model data storage section 50 (S411).

It is assumed to be confirmed that the value la is greater than the value indicated by the total posterior arm length data stored in the skeleton model data storage section 50 (S411: Y). In this case, the posture update section 56 updates the total posterior arm length data stored in the skeleton model data storage section 50 so that the total posterior arm length data indicates the estimated value la of the total posterior arm length calculated in the processing illustrated in S410 (S412).

The posture update section 56 then updates the transverse body size data stored in the skeleton model data storage section 50 so that the transverse body size data indicates a sum of a double of the value of the total posterior arm length data and the value of the shoulder length is described above (S413). The posture update section 56 then returns to the processing illustrated in S401.

It is noted that the posture update section 56 returns to the processing illustrated in S401 even in a case in which it is confirmed that the difference between the length from the position T2 to the position psl and the length from the position T3 to the position psr is not equal to or smaller than the predetermined threshold t2 in the processing illustrated in S409 (S409: N). In this case, the processing illustrated in S410 to S413 is skipped since there is a high probability that the value indicating the position T2 and the value indicating the position T3 are abnormal values based on an error. Further, the posture update section 56 returns to the processing illustrated in S401 even in a case in which it is confirmed that the value la is not greater than the value of the total posterior arm length indicated by the total posterior arm length data stored in the skeleton model data storage section 50 in the processing illustrated in S411 (S411: N).

For example, as the value of the right-foot-based head position data D2 and the value of the left-foot-based head position data D3, values each obtained by dividing the coordinate values of the position of the head based on the position of each foot by the value of body height size data, the value of the total posterior arm length, or the value of the transverse body size data stored in the skeleton model data storage section 50 may be used.

Further, the processing illustrated in S401 to S413 described above may be executed in the learning of the machine learning model depicted in FIG. 13. In addition, as the value of the right-foot-based head position data D2 and the value of the left-foot-based head position data D3, values each obtained by dividing the coordinate values of the position of the head based on the position of each foot by the value of the body height size data, the value of the total posterior arm length, or the value of the transverse body size data may be used.

It is noted that the present invention is not limited to the embodiment described above.

For example, an applicable range of the present invention is not limited to the update of the posture of the skeleton model 40 in real time according to actual motions of the trackers 12. The present invention may be applied to, for example, a scene for reproducing the skeleton model 40 or a state in which a player object according to the skeleton model 40 moves, on the basis of time series of a series of pieces of posture data that is recorded in the entertainment apparatus 14 in advance.

Further, the tracker 12a, for example, may be a head mounted display (HMD). In this case, a video picture according to a result of various types of processing such as game processing according to the positions or the directions of the plurality of regions included in the user may be displayed on, for example, a display section of the HMD.

Further, part of or entirety of the functions depicted in FIG. 6 may be implemented by the trackers 12.

Further, specific character strings and numeric values described above and specific character strings and numeric values in the drawings are given as an example and the present invention is not limited to these character strings and numeric values.

The invention claimed is:

1. A skeleton model update apparatus comprising:
a posture data acquisition section that acquires posture data indicating a posture of a first target node and a posture of a second target node, the first and second target nodes being included in a skeleton model of a tree structure;
a first posture update section that performs update of postures of a first node group that contains nodes including the first target node and connected to one another by forward reaching phase processing in Forward and Backward Reaching Inverse Kinematics computing, on the first node group on a basis of the posture data;
a second posture update section that performs update of postures of a second node group that contains nodes including the second target node and connected to one another by the forward reaching phase processing in the Forward and Backward Reaching Inverse Kinematics computing, on the second node group on the basis of the posture data;
a third posture update section that updates postures of a plurality of nodes including a node included in the first node group and closest to a junction included in the skeleton model and a node included in the second node group and closest to a junction included in the skeleton model after updating the first node group and the second node group; and
a fourth posture update section that updates a posture of the skeleton model by backward reaching phase processing in the Forward and Backward Reaching Inverse Kinematics computing.

2. The skeleton model update apparatus according to claim 1, further comprising: an estimation section that estimates a pivoting foot on the basis of the posture data; and a determination section that determines an initial position of a lumbar node in the Forward and Backward Reaching Inverse Kinematics computing on a basis of a position of the pivoting foot.

3. The skeleton model update apparatus according to claim 2, wherein
the estimation section further estimates whether a user is in a seated posture or a standing posture, and
the estimation section estimates the pivoting foot in a case of estimating that the user is in the standing posture.

4. A skeleton model update method comprising:
acquiring posture data indicating a posture of a first target node and a posture of a second target node, the first and second target nodes being included in a skeleton model of a tree structure;
performing update of postures of a first node group that contains nodes including the first target node and connected to one another by forward reaching phase processing in Forward and Backward Reaching Inverse Kinematics computing, on the first node group on a basis of the posture data;
performing update of postures of a second node group that contains nodes including the second target node and connected to one another by the forward reaching phase processing in the Forward and Backward Reaching Inverse Kinematics computing, on the second node group on the basis of the posture data;
updating postures of a plurality of nodes including a node included in the first node group and closest to a junction included in the skeleton model and a node included in the second node group and closest to a junction included in the skeleton model after updating the first node group and the second node group; and updating a posture of the skeleton model by backward reaching phase processing in the Forward and Backward Reaching Inverse Kinematics computing.

5. A non-transitory computer readable medium having stored thereon a program for a computer, comprising:

by a posture data acquisition section, acquiring posture data indicating a posture of a first target node and a posture of a second target node, the first and second target nodes being included in a skeleton model of a tree structure;

by a first posture update section, performing update of postures of a first node group that contains nodes including the first target node and connected to one another by forward reaching phase processing in Forward and Backward Reaching Inverse Kinematics computing, on the first node group on a basis of the posture data;

by a second posture update section, performing update of postures of a second node group that contains nodes including the second target node and connected to one another by the forward reaching phase processing in the Forward and Backward Reaching Inverse Kinematics computing, on the second node group on the basis of the posture data;

by a third posture update section, updating postures of a plurality of nodes including a node included in the first node group and closest to a junction included in the skeleton model and a node included in the second node group and closest to a junction included in the skeleton model after updating the first node group and the second node group; and by a fourth posture update section, updating a posture of the skeleton model by backward reaching phase processing in the Forward and Backward Reaching Inverse Kinematics computing.

* * * * *